United States Patent [19]

Cai et al.

[11] Patent Number: 5,244,883
[45] Date of Patent: Sep. 14, 1993

[54] NONAPEPTIDE BOMBESIN ANTAGONISTS

[75] Inventors: Renzhi Cai; Andrew V. Schally, both of Metairie, La.

[73] Assignee: The Administrators of the Tulane Educational Fund, New Orleans, La.

[21] Appl. No.: 619,747

[22] Filed: Nov. 29, 1990

[51] Int. Cl.$^5$ .................. A61K 37/00; A61K 37/02; C07K 5/00; C07K 7/00

[52] U.S. Cl. .................. 514/15; 530/327; 530/328; 514/14

[58] Field of Search .................. 514/15, 14; 530/328, 530/327

[56] References Cited

FOREIGN PATENT DOCUMENTS 0339193 2/1989 European Pat. Off. .
90/01037 2/1990 PCT Int'l Appl. .
90/03980 4/1990 PCT Int'l Appl. .

OTHER PUBLICATIONS

Coy et al., J. of Biol. Chem., vol. 264, No. 25, pp. 14691-14697, Sep. 1989.
Coy et al., J. Biol. Chem., vol. 263, No. 11, pp. 5056-5060, Apr. 1988.
Smith et al., Principles of Biochemistry 7th ed., edoted. Laufer et al., McGraw-Hill, New York, 1983.

Primary Examiner—Lester L. Lee
Assistant Examiner—A. M. Davenport
Attorney, Agent, or Firm—Omri M. Behr; Matthew J. McDonald

[57] ABSTRACT

The novel pseudo polypeptides of this invention are potent bombesin antagonists. There are provided processes for their production, pharmaceutical compositions comprising said polypeptides and their use as pharmaceutically active agents. More particularly the present invention provides pseudopeptides comprising a nonapeptide moiety of formula I:

$$X-A^1-A^2-A^3-A^4-A^5-A^6-A^7-A^8-_{psi}-A^9-Q$$

wherein Q is $NH_2$ or $OQ^1$ where $Q^1$ is hydrogen, $C_{1-10}$ alkyl, phenyl or phenyl-$C_{7-10}$alkyl; X is hydrogen or a single bond linking to $A^2$ the acyl residue of an organic acid, or a group of formula $R^1CO-$ wherein (1) $R^1$ is hydrogen, $C_{1-10}$ alkyl, phenyl or phenyl-$C_{7-10}$-alkyl; (2) $R^1CO-$ is (a) $R^2N(R^3)-CO-$ wherein $R^2$ is hydrogen, $C_{1-10}$alkyl, phenyl or $C_{7-10}$phenyl-$C_{7-10}$-alkyl, $R^3$ is hydrogen or $C_{1-10}$alkyl; (b) $R^4-O-CO-$ wherein $R^4$ is $C_{1-10}$alkyl, phenyl or phenyl-$C_{7-10}$-alkyl. $A^1$ is D-, L- or DL- pGlu,, Nal, Phe, Thl, Tyr, Tpi, Hca, Hpp, Mpp, Trp or Trp substituted in the benzene ring by one or more members selected from the group consisting of halogen, $NO_2$, $NH_2$, OH, $C_{1-3}$ alkyl and $C_{1-3}$ alkoxy wherein halogen is fluorine, chlorine and bromine; wherein $A^2-A^7$ and $A^9$ are each amino acid residues; $A^8$ is a reduced isostere of Leu or Phe.

20 Claims, No Drawings

SEQUENCE LISTING ( 1 ) GENERAL INFORMATION:

( i i i ) NUMBER OF SEQUENCES: 40

( 2 ) INFORMATION FOR SEQ ID NO: 1:

( i ) SEQUENCE CHARACTERISTICS:
 ( A ) LENGTH: 9
 ( B ) TYPE:Amino
 ( C ) STRANDEDNESS:Unknown
 ( D ) TOPOLOGY:Unknown ( i i ) MOLECULE TYPE: peptide ( i x ) FEATURE:
 ( D ) OTHER INFORMATION: Position 8 is a reduced
 isostere of named aminoacid ( x i ) SEQUENCE DESCRIPTION: SEQ ID NO: 1:

Trp  Gln  Trp  Ala  Val  Gly  His  Leu  Leu
 1              5                        9

( 2 ) INFORMATION FOR SEQ ID NO: 2:

( i ) SEQUENCE CHARACTERISTICS:
 ( A ) LENGTH: 9
 ( B ) TYPE:Amino
 ( C ) STRANDEDNESS:Unknown (D) TOPOLOGY:Unknown (i i) MOLECULE TYPE: peptide (i x) FEATURE:
    (D) OTHER INFORMATION: Position 1 is D-Trp
                                            Position 8 is a reduced
                                            isostere of named aminoacid (x i) SEQUENCE DESCRIPTION: SEQ ID NO: 2:

Xaa Gln Trp Ala Val Gly His Leu Leu
1              5                   9

(2) INFORMATION FOR SEQ ID NO: 3:

(i) SEQUENCE CHARACTERISTICS:
    (A) LENGTH: 9
    (B) TYPE:Amino
    (C) STRANDEDNESS:Unknown
    (D) TOPOLOGY:Unknown (i i) MOLECULE TYPE: peptide (i x) FEATURE:
    (D) OTHER INFORMATION: Position 1 is D-Trp
                                            Position 2 is Glu(MeNH)
                                            Position 8 is a reduced
                                            isostere of named aminoacid (x i) SEQUENCE DESCRIPTION: SEQ ID NO: 3:

Xaa Glu Trp Ala Val Gly His Leu Leu
1              5                   9

(2) INFORMATION FOR SEQ ID NO: 4:

(i) SEQUENCE CHARACTERISTICS:
    (A) LENGTH: 9
    (B) TYPE:Amino
    (C) STRANDEDNESS:Unknown
    (D) TOPOLOGY:Unknown (i i) MOLECULE TYPE: peptide (i x) FEATURE:
    (D) OTHER INFORMATION: Position 1 is 5F-D-Trp
                                            Position 8 is a reduced
                                            isostere of named aminoacid (x i) SEQUENCE DESCRIPTION: SEQ ID NO: 4:

Xaa Gln Trp Ala Val Gly His Leu Leu
1              5                   9

(2) INFORMATION FOR SEQ ID NO: 5:

(i) SEQUENCE CHARACTERISTICS:
    (A) LENGTH: 9
    (B) TYPE:Amino
    (C) STRANDEDNESS:Unknown
    (D) TOPOLOGY:Unknown (i i) MOLECULE TYPE: peptide (i x) FEATURE:
    (D) OTHER INFORMATION: Position 1 is D-Tpi
                                            Position 8 is a reduced
                                            isostere of named aminoacid (x i) SEQUENCE DESCRIPTION: SEQ ID NO: 5:

Xaa Gln Trp Ala Val Gly His Leu Leu
1              5                   9

(2) INFORMATION FOR SEQ ID NO: 6:

-continued (i) SEQUENCE CHARACTERISTICS:
    (A) LENGTH: 9
    (B) TYPE: Amino
    (C) STRANDEDNESS: Unknown
    (D) TOPOLOGY: Unknown (ii) MOLECULE TYPE: peptide (ix) FEATURE:
    (D) OTHER INFORMATION: Position 1 is D-Tpi
        Position 2 is Glu(OMe)
        Position 8 is a reduced
        isostere of named aminoacid (xi) SEQUENCE DESCRIPTION: SEQ ID NO: 6:

Xaa Glu Trp Ala Val Gly His Leu Leu
 1               5               9

(2) INFORMATION FOR SEQ ID NO: 7:

(i) SEQUENCE CHARACTERISTICS:
    (A) LENGTH: 9
    (B) TYPE: Amino
    (C) STRANDEDNESS: Unknown
    (D) TOPOLOGY: Unknown (ii) MOLECULE TYPE: peptide (ix) FEATURE:
    (D) OTHER INFORMATION: Position 1 is D-Tpi
        Position 8 is a reduced
        isostere of named aminoacid (xi) SEQUENCE DESCRIPTION: SEQ ID NO: 7:

Xaa His Trp Ala Val Gly His Leu Leu
 1               5               9

(2) INFORMATION FOR SEQ ID NO: 8:

(i) SEQUENCE CHARACTERISTICS:
    (A) LENGTH: 9
    (B) TYPE: Amino
    (C) STRANDEDNESS: Unknown
    (D) TOPOLOGY: Unknown (ii) MOLECULE TYPE: peptide (ix) FEATURE:
    (D) OTHER INFORMATION: Position 1 is D-Tpi
        Position 2 is His(Bz)
        Position 8 is a reduced
        isostere of named aminoacid (xi) SEQUENCE DESCRIPTION: SEQ ID NO: 8:

Xaa His Trp Ala Val Gly His Leu Leu
 1               5               9

(2) INFORMATION FOR SEQ ID NO: 9:

(i) SEQUENCE CHARACTERISTICS:
    (A) LENGTH: 9
    (B) TYPE: Amino
    (C) STRANDEDNESS: Unknown
    (D) TOPOLOGY: Unknown (ii) MOLECULE TYPE: peptide (ix) FEATURE:
    (D) OTHER INFORMATION: Position 1 is NH2CO-Trp
        Position 8 is a reduced
        isostere of named aminoacid (xi) SEQUENCE DESCRIPTION: SEQ ID NO: 9:

Trp Gln Trp Ala Val Gly His Leu Phe
 1               5               9

( 2 ) INFORMATION FOR SEQ ID NO: 10:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is D-Trp
                Position 8 is a reduced
                isostere of named aminoacid ( x i ) SEQUENCE DESCRIPTION: SEQ ID NO: 10:

Xaa Gln Trp Ala Val Gly His Leu Phe
    1                 5                 9

( 2 ) INFORMATION FOR SEQ ID NO: 11:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is D-Trp
                Position 2 is Glu(MeNH)
                Position 8 is a reduced
                isostere of named aminoacid ( x i ) SEQUENCE DESCRIPTION: SEQ ID NO: 11:

Xaa Glu Trp Ala Val Gly His Leu Phe
    1                 5                 9

( 2 ) INFORMATION FOR SEQ ID NO: 12:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is D-Tpi
                Position 8 is a reduced
                isostere of named aminoacid ( x i ) SEQUENCE DESCRIPTION: SEQ ID NO: 12:

Xaa Gln Trp Ala Val Gly His Leu Phe
    1                 5                 9

( 2 ) INFORMATION FOR SEQ ID NO: 13:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is D-Tpi
                Position 2 is Glu(OMe)
                Position 8 is a reduced
                isostere of named aminoacid ( x i ) SEQUENCE DESCRIPTION: SEQ ID NO: 13:

Xaa Glu Trp Ala Val Gly His Leu Phe
1             5                   9

( 2 ) INFORMATION FOR SEQ ID NO: 14:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is Hca
        Position 8 is a reduced
        isostere of named aminoacid
        Position 9 is Tpi ( x i ) SEQUENCE DESCRIPTION: SEQ ID NO: 14:

Xaa Gln Trp Ala Val Gly His Leu Xaa
1             5                   9

( 2 ) INFORMATION FOR SEQ ID NO: 15:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION:Position 1 is D-pGlu
        Position 8 is a reduced
        isostere of named aminoacid
        Position 9 is Tpi ( x i ) SEQUENCE DESCRIPTION: SEQ ID NO: 15:

Xaa Gln Trp Ala Val Gly His Leu Xaa
1             5                   9

( 2 ) INFORMATION FOR SEQ ID NO: 16:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 8 is a reduced
        isostere of named amino acid ( x i ) SEQUENCE DESCRIPTION: SEQ ID NO: 16:

Phe Glu Trp Ala Val Gly His Leu Trp
1             5                   9

( 2 ) INFORMATION FOR SEQ ID NO: 17:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is D-Phe Position 8 is a reduced
isostere of named aminoacid ( x i ) SEQUENCE DESCRIPTION: SEQ ID NO: 17:

Xaa Gln Trp Ala Val Gly His Leu Trp
1             5                   9

( 2 ) INFORMATION FOR SEQ ID NO: 18:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is D-Trp
                Position 8 is a reduced
                isostere of named aminoacid
                Position 9 is Tpi ( x i ) SEQUENCE DESCRIPTION: SEQ ID NO: 18:

Xaa Gln Trp Ala Val Gly His Leu Xaa
1             5                   9

( 2 ) INFORMATION FOR SEQ ID NO: 19:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is D-Trp
                Position 8 is a reduced
                isostere of named aminoacid
                Position 9 is Tpi ( x i ) SEQUENCE DESCRIPTION: SEQ ID NO: 19:

Xaa His Trp Ala Val Gly His Leu Xaa
1             5                   9

( 2 ) INFORMATION FOR SEQ ID NO: 20:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is D-Trp
                Position 8 is a reduced
                isostere of named aminoacid
                Position 9 is Tpi ( x i ) SEQUENCE DESCRIPTION: SEQ ID NO: 20:

Xaa Glu Trp Ala Val Gly His Leu Xaa
1             5                   9

( 2 ) INFORMATION FOR SEQ ID NO: 21:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
    ( D ) OTHER INFORMATION: Position 1 is D-Trp; 2 is
            Glu(OMe); 9 is Tpi
            Position 8 is a reduced
            isostere of named aminoacid ( x i ) SEQUENCE DESCRIPTION: SEQ ID NO: 21:

Xaa Glu Trp Ala Val Gly His Leu Xaa
1             5             9

( 2 ) INFORMATION FOR SEQ ID NO: 22:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is Tpi
                Position 8 is a reduced
                isostere of named aminoacid
                Position 9 is Tpi ( x i ) SEQUENCE DESCRIPTION: SEQ ID NO: 22:

Xaa Gln Trp Ala Val Gly His Leu Xaa
1             5             9

( 2 ) INFORMATION FOR SEQ ID NO: 23:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is Ac-Tpi
                Position 8 is reduced
                isostere of named aminoacid
                Position 9 is Tpi ( x i ) SEQUENCE DESCRIPTION: SEQ ID NO: 23:

Xaa Gln Trp Ala Val Gly His Leu Xaa
1             5             9

( 2 ) INFORMATION FOR SEQ ID NO: 24:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is NH2CO-Tpi
                Position 8 is reduced
                isostere of named aminoacid
                Position 9 is Tpi ( x i ) SEQUENCE DESCRIPTION: SEQ ID NO: 24:

Xaa Gln Trp Ala Val Gly His Leu Xaa
1             5             9

( 2 ) INFORMATION FOR SEQ ID NO: 25:

( i ) SEQUENCE CHARACTERISTICS:
    ( A ) LENGTH: 9
    ( B ) TYPE: Amino
    ( C ) STRANDEDNESS: Unknown
    ( D ) TOPOLOGY: Unknown ( i i ) MOLECULE TYPE: peptide ( i x ) FEATURE:
    ( D ) OTHER INFORMATION: Position 1 is Hna-Tpi
                             Position 8 is a reduced
                             isostere of named aminoacid
                             Position 9 is Tpi ( x i ) SEQUENCE DESCRIPTION: SEQ ID NO: 25:

Xaa Gln Trp Ala Val Gly His Leu Xaa
 1               5                9

( 2 ) INFORMATION FOR SEQ ID NO: 26:

( i ) SEQUENCE CHARACTERISTICS:
        ( A ) LENGTH: 9
        ( B ) TYPE: Amino
        ( C ) STRANDEDNESS: Unknown
        ( D ) TOPOLOGY: Unknown ( i i ) MOLECULE TYPE: peptide ( i x ) FEATURE:
        ( D ) OTHER INFORMATION: Position 1 is D-Tpi
                                 Position 8 is a reduced
                                 isostere of named aminoacid
                                 Position 9 is Tpi ( x i ) SEQUENCE DESCRIPTION: SEQ ID NO: 26:

Xaa Gln Trp Ala Val Gly His Leu Xaa
 1               5                9

( 2 ) INFORMATION FOR SEQ ID NO: 27:

( i ) SEQUENCE CHARACTERISTICS:
        ( A ) LENGTH: 9
        ( B ) TYPE: Amino
        ( C ) STRANDEDNESS: Unknown
        ( D ) TOPOLOGY: Unknown ( i i ) MOLECULE TYPE: peptide ( i x ) FEATURE:
        ( D ) OTHER INFORMATION: Position 1 is Mpp
                                 Position 8 is a reduced
                                 isostere of named aminoacid ( x i ) SEQUENCE DESCRIPTION: SEQ ID NO: 27:

Xaa Gln Trp Ala Val Gly His Leu Trp
 1               5                9

( 2 ) INFORMATION FOR SEQ ID NO: 28:

( i ) SEQUENCE CHARACTERISTICS:
        ( A ) LENGTH: 9
        ( B ) TYPE: Amino
        ( C ) STRANDEDNESS: Unknown
        ( D ) TOPOLOGY: Unknown ( i i ) MOLECULE TYPE: peptide ( i x ) FEATURE:
        ( D ) OTHER INFORMATION: Position 1 is D-Phe
                                 Position 8 is a reduced
                                 isostere of named aminoacid ( x i ) SEQUENCE DESCRIPTION: SEQ ID NO: 28:

Xaa Gln Trp Ala Val Gly His Leu Trp (2) INFORMATION FOR SEQ ID NO: 29:

(i) SEQUENCE CHARACTERISTICS:
        (A) LENGTH: 9
        (B) TYPE: Amino
        (C) STRANDEDNESS: Unknown
        (D) TOPOLOGY: Unknown (ii) MOLECULE TYPE: peptide (ix) FEATURE:
        (D) OTHER INFORMATION: Position 1 is D-Trp
        Position 8 is a reduced
        isostere of named aminoacid (xi) SEQUENCE DESCRIPTION: SEQ ID NO: 29:

Xaa Gln Trp Ala Val Gly His Leu Trp
1               5                   9

(2) INFORMATION FOR SEQ ID NO: 30:

(i) SEQUENCE CHARACTERISTICS:
        (A) LENGTH: 9
        (B) TYPE: Amino
        (C) STRANDEDNESS: Unknown
        (D) TOPOLOGY: Unknown (ii) MOLECULE TYPE: peptide (ix) FEATURE:
        (D) OTHER INFORMATION: Position 1 is D-Tpi
        Position 8 is a reduced
        isostere of named aminoacid (xi) SEQUENCE DESCRIPTION: SEQ ID NO: 30:

Xaa Gln Trp Ala Val Gly His Leu Trp
1               5                   9

(2) INFORMATION FOR SEQ ID NO: 31:

(i) SEQUENCE CHARACTERISTICS:
        (A) LENGTH: 9
        (B) TYPE: Amino
        (C) STRANDEDNESS: Unknown
        (D) TOPOLOGY: Unknown (ii) MOLECULE TYPE: peptide (ix) FEATURE:
        (D) OTHER INFORMATION: Position 1 Mpp
        Position 8 is a reduced
        isostere of named aminoacid
        Position 9 is Trp(For)

(xi) SEQUENCE DESCRIPTION: SEQ ID NO: 31:

Xaa Gln Trp Ala Val Gly His Leu Xaa
1               5                   9

(2) INFORMATION FOR SEQ ID NO: 32:

(i) SEQUENCE CHARACTERISTICS:
        (A) LENGTH: 9
        (B) TYPE: Amino
        (C) STRANDEDNESS: Unknown
        (D) TOPOLOGY: Unknown (ii) MOLECULE TYPE: peptide (ix) FEATURE:
        (D) OTHER INFORMATION: Position 1 is D-Phe
        Position 8 is a reduced
        isostere of named aminoacid
        Position 9 is Trp(For)

( x i ) SEQUENCE DESCRIPTION: SEQ ID NO: 32:

Xaa Gln Trp Ala Val Gly His Leu Xaa
1              5                   9

( 2 ) INFORMATION FOR SEQ ID NO: 33:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is D-Trp
                Position 8 is a reduced
                isostere of named aminoacid
                Position 9 is Trp(For)

( x i ) SEQUENCE DESCRIPTION: SEQ ID NO: 33:

Xaa Gln Trp Ala Val Gly His Leu Xaa
1              5                   9

( 2 ) INFORMATION FOR SEQ ID NO: 34:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is D-Tpi
                Position 8 is a reduced
                isostere of named aminoacid
                Position 9 is Trp(For)

( x i ) SEQUENCE DESCRIPTION: SEQ ID NO: 34:

Xaa Gln Trp Ala Val Gly His Leu Xaa
1              5                   9

( 2 ) INFORMATION FOR SEQ ID NO: 35:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
        ( D ) OTHER INFORMATION: Position 1 is Tpi
                Position 8 is a reduced
                isostere of named aminoacid
                Position 9 is Tpi-OMe ( x i ) SEQUENCE DESCRIPTION: SEQ ID NO: 35:

Xaa Gln Trp Ala Val Gly His Leu Xaa
1              5                   9

( 2 ) INFORMATION FOR SEQ ID NO: 36:

( i ) SEQUENCE CHARACTERISTICS:
        ( A ) LENGTH: 9
        ( B ) TYPE:Amino
        ( C ) STRANDEDNESS:Unknown
        ( D ) TOPOLOGY:Unknown ( i i ) MOLECULE TYPE: peptide ( i x ) FEATURE:
    ( D ) OTHER INFORMATION: Position 1 is D-Tpi
        Position 8 is a reduced
        isostere of named aminoacid
        Position 9 is Tpi-OMe ( x i ) SEQUENCE DESCRIPTION: SEQ ID NO: 36:

Xaa Gln Trp Ala Val Gly His Leu Xaa
1               5               9

( 2 ) INFORMATION FOR SEQ ID NO: 37:

( i ) SEQUENCE CHARACTERISTICS:
    ( A ) LENGTH: 9
    ( B ) TYPE: Amino
    ( C ) STRANDEDNESS: Unknown
    ( D ) TOPOLOGY: Unknown ( i i ) MOLECULE TYPE: peptide ( i x ) FEATURE:
    ( D ) OTHER INFORMATION: Position 1 is NH2CO-Tpi
        Position 8 is a reduced
        isostere of named aminoacid
        Position 9 is Tpi-OMe ( x i ) SEQUENCE DESCRIPTION: SEQ ID NO: 37:

Xaa Gln Trp Ala Val Gly His Leu Xaa
1               5               9

( 2 ) INFORMATION FOR SEQ ID NO: 38:

( i ) SEQUENCE CHARACTERISTICS:
    ( A ) LENGTH: 9
    ( B ) TYPE: Amino
    ( C ) STRANDEDNESS: Unknown
    ( D ) TOPOLOGY: Unknown ( i i ) MOLECULE TYPE: peptide ( i x ) FEATURE:
    ( D ) OTHER INFORMATION: Position 1 is D-Tpi
        Position 8 is a reduced
        isostere of named aminoacid
        Position 9 is Tpi ( x i ) SEQUENCE DESCRIPTION: SEQ ID NO: 38:

Xaa Gln Trp Ala Val Gly His Leu Xaa
1               5               9

( 2 ) INFORMATION FOR SEQ ID NO: 39:

( i ) SEQUENCE CHARACTERISTICS:
    ( A ) LENGTH: 9
    ( B ) TYPE: Amino
    ( C ) STRANDEDNESS: Unknown
    ( D ) TOPOLOGY: Unknown ( i i ) MOLECULE TYPE: peptide ( i x ) FEATURE:
    ( D ) OTHER INFORMATION: Position 1 is D-Tpi
        Position 8 is reduced
        isostere of named aminoacid
        Position 9 is Tpi-OH ( x i ) SEQUENCE DESCRIPTION: SEQ ID NO: 39:

Xaa Gln Trp Ala Val Gly His Leu Xaa
1               5               9

( 2 ) INFORMATION FOR SEQ ID NO: 40:

( i ) SEQUENCE CHARACTERISTICS:
    ( A ) LENGTH: 9

(B) TYPE: Amino
(C) STRANDEDNESS: Unknown
(D) TOPOLOGY: Unknown (i i) MOLECULE TYPE: peptide (i x) FEATURE:
  (D) OTHER INFORMATION: Position 1 is D-Tpi
    Position 8 is a reduced
    isostere of named aminoacid
    Position 9 is Tpi-N2H2CONH2

(x i) SEQUENCE DESCRIPTION: SEQ ID NO: 40:

Xaa Gln Trp Ala Val Gly His Leu Xaa
 1           5               9

NONAPEPTIDE BOMBESIN ANTAGONISTS

This invention was made with Government support under grant No. CA 40077, awarded by the N.C.I. (NIH). The U.S. Government has certain rights in this application.

FIELD OF THE INVENTION

The present invention is directed to novel peptides which influence the growth of cancerous tumors in humans. More specifically, the present invention relates to bombesin antagonists which are [8-9 pseudo] nonapeptides containing a D- or L tryptophan or tryptophan analog 2,3,4,9-tetrahydro-1H-pyrido[3,4-b]indol-3-carboxylic acid (Tpi) at the N or/and the C-terminal which possess antagonist properties against bombesin or bombesin-like peptides the salts thereof, and pharmaceutical compositions and methods of use pertaining to these peptides.

BACKGROUND OF THE INVENTION

The invention relates to polypeptide compounds which possess antagonist properties against bombesin or bombesin-like peptides such as gastrin releasing peptide (GRP), Neuromedin C and the like, hereinafter referred to as bombesin antagonist properties and are of value, for example in the treatment of malignant disease in warm-blooded animals such as man. The invention includes novel polypeptide compounds and processes for their manufacture; novel pharmaceutical compositions containing said polypeptide compounds and processes for the manufacture of medicaments containing them for use in producing a bombesin antagonist effect in warm-blooded animals such as man.

Bombesin is a tetradecapeptide amide which was first isolated from the skin of the frog Bombina - bombina (Anastasi, Erspamer and Bucci, *Experientia*, 1971, 27, 166). It is known that bombesin is a potent mitogen for mouse Swiss 3T3 fibroblast cells (Rozengurt and Sinnett-Smith, *Proc. Natl. Acad. Sci. U.S.A.*, 1983, 80, 2936) and that it stimulates amylase secretion from guinea pig pancreatic acini (Jensen, Jones, Folkers and Gardner, *Nature*, 1984, 309, 61). It is also known that bombesin-like peptides are produced and secreted by human small-cell lung cancer (SCLC) cells (Moody, Pert, Gazdar, Carney and Minna, *Science*, 1981, 214, 1246), that exogenously added bombesin-like peptides can stimulate the growth of human SCLC cells in vitro (Carney, Cuttita, Moody and Minna, *Cancer Research*, 1987, 47, 821) and that a monoclonal antibody specific for the C-Terminal region of bombesin and GRP can block binding of GRP to its receptors and prevent the growth of human SCLC cells both in vitro and in vivo (Cuttita, Carney, Mulshine, Moody, Fedorko, Fischler and Minna, *Nature*, 1985, 3167, 823).

GRP which has bombesin-like properties is a widely distributed peptide amide containing 27 amino-acid isolated from the porcine gut (McDonald, Jornvall, Nilsson, Vagne, Ghatei, Bloom and Mutt, *Biochem. Biophys. Biophys. Res. Commun.*, 1979, 90, 227) in which the C-terminal amino acid sequence is almost identical to that of bombesin. Neuromedin C is a decapeptide amide, the structure of which is identical to the last ten amino acids in the C-terminus region of GRP, which has been isolated from the canine small intestine (Reeve, Walsh, Chew, Clark, Hawke and Shively, *J. Biol. Chem.*, 1983, 258, 5582). GRP stimulates a variety of biological responses, including the release of gastrin in the systemic circulation. It also functions as a growth factor in 3T3 mouse fibroblasts and small cell lung cancer (SCLC) cell. So GRP has been proposed to play a direct pathophysiological role in the development of SCLC via an autocrine growth mechanism.

The structures of bombesin, Neuromedin C and Carboxyl-terminal nonapeptide of GRP are shown below:
Bombesin: pGlu-Gln-Arg-Leu-Gly-Asn-Gln-Trp-Ala-Val-Gly-His-Leu- Met-NH$_2$
Neuromedin C: H-Gly-Asn-His-Trp-Ala-Val-Gly-His-Leu-Met-NH$_2$
C-terminal nonapeptide of GRP: -Asn-His-Trp-Ala-Val-Gly-His-Leu-Met-NH$_2$ The search for other amphibian bombesin-like peptides led to the isolation of Litorin a nonapeptide (pGlu-Gln-Trp-Ala-Val-Gly-His-Leu-Met-NH$_2$) in the skin of frog from Papua, New Guinea which proves to be the most potent bombesin (Yasukara et al., Chem. Pharm. Bull., 1979, 27, 492). The studies on bombesin analogues showed that a minimum segment of the 9 amino acid residues from 6-14 position of bombesin possessed the full spectrum of bombesin activity.

Several kinds of bombesin antagonists are now known. Substance P (Arg-Pro-Lys-Pro-Gln-Gln-Phe-Phe-Gly-Leu-Met-NH$_2$) which has slight amino acid sequence homology with bombesin does not inhibit the binding of bombesin and bombesin-like peptides, but substance P analogues modified by the replacement of several of L-amino acids with D-amino acids such as (D-Arg$^1$, D-Pro$^2$, D-Trp$^{7,9}$, Leu$^{11}$) Substance P and (D-Arg$^1$, D-Phe$^5$, D-Trp$^{7,9}$, Leu$^{11}$) Substance P, (Moody et al., Fed. Proceedings, 1987, 46, 2201) were found to block the secreting of bombesin in pancreatic acinar cells and to antagonize the growth-promoting effects of bombesin in Swiss 3T3 cells. Two types of bombesin antagonists derived from bombesin, for instance, (D-Phe$^5$, D-Phe$^{12}$) bombesin, and [Leu$^{13}$-$psi$-Leu$^{14}$] bombesin (Coy et al., *J. Biol. Chem.*, 1988, 263, 5056 and peptides, 1989, 10, 587) have proved to be potent in vitro and in vivo inhibitors of bombesin response.

Another type of bombesin antagonist revealed by Heimbrook et al., (Bio. Chem., 1989, 264, 11258) is N-acetyl-GRP(20-26) and its analogous wherein the C-terminal methionine residue is deleted from GRP(20-27) analogues. Recently, Coy [*J. Biol. Chem.* 264, 1989, 25, 14691] reported that some short chain bombesin antagonists based on Litorin sequence such as [D-Phe$^6$, Leu$^{13}$-$psi$-Phe$^{14}$] bombesin-(6-14) and [D-Phe$^6$, Leu$^{13}$-$psi$-Leu$^{14}$] bombesin-(6-14) exhibited much more potency than their corresponding parent peptide [Leu$^{13}$-$psi$-Leu$^{14}$] bombesin.

SUMMARY OF THE INVENTION

The present invention provides novel polypeptides which are potent bombesin antagonists, processes for their production, pharmaceutical compositions comprising said polypeptides and their use as pharmaceutically active agents.

More particularly the present invention provides pseudopeptides comprising a nonapeptide moiety of formula I:

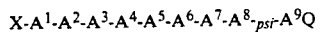

wherein

Q is $NH_2$ or $OQ^1$ where $Q^1$ is hydrogen, $C_{1-10}$ alkyl, phenyl or phenyl-$C_{7-10}$-alkyl;

X is hydrogen or a single bond linking to $A^2$, the acyl residue of an organic acid, or a group of formula $R^1CO$— wherein
(1) $R^1$ is hydrogen, $C_{1-10}$ alkyl, phenyl or phenyl-$C_{7-10}$-alkyl;
(2) $R^1CO$— is

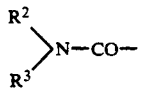
(a)

wherein
$R^2$ is hydrogen, $C_{1-10}$ alkyl, phenyl or $C_{7-10}$ phenyl-$C_{7-10}$-alkyl, $R^3$ is hydrogen or $C_{1-10}$ alkyl;

(b) $R^4$—O—CO— wherein $R^4$ is $C_{1-10}$alkyl, phenyl or phenyl-$C_{7-10}$-alkyl.

$A^1$ is D-, L- or DL- pGlu, Nal, Phe, Thi, Tyr, Tpi, Hca, Hpp, Mpp, Trp or Trp substituted in the benzene ring by one or more members selected from the group consisting of halogen, $NO_2$, $NH_2$, OH, $C_{1-3}$ alkyl and $C_{1-3}$ alkoxy wherein halogen is fluorine, chlorine and bromine.

$A^2$ is Asn, Dpa, Gln, His, MeHis, His(Bz), His(Z) or a group of formula Dpa (X), Asp (Y), Glu [—] and Glu (Y). wherein
X is as above,
Y is —$OR^5$ or

wherein
$R^5$ is hydrogen, $C_{1-3}$ alkyl or phenyl;
$R^6$ is hydrogen or $C_{1-3}$ alkyl;
$R^7$ is hydrogen, $C_{1-3}$ alkyl or —$NHCONH_2$ and
[—] is a single bond linking the side carboxyl group with the alpha amino group of $A^1$ where X is a single bond.

$A^3$ is Nal, Pal, Tpi, Trp, MeTrp, Trp(For) or Trp substituted in the benzene ring by one or more members selected from the group consisting of halogen, $NO_2$, $NH_2$, OH, $C_{1-3}$ alkyl and $C_{1-3}$ alkoxy wherein halogen is fluorine, chlorine and bromine;
$A^4$ is Ala, MeAla or Gln;
$A^5$ is Val or MeVal;
$A^6$ is Gly, Phe or D-Ala;
$A^7$ is His, MeHis, His(Bz), His(Z), Lys(Z) or Pal;
$A^8$ is reduced isostere of Leu or Phe;
$A^9$ is Leu, Phe, Tpi, Trp or Trp substituted in the benzene ring by one or more members selected from the group consisting of halogen, $NO_2$, $NH_2$, OH, $C_{1-3}$ alkyl and $C_{1-3}$ alkoxy wherein halogen is fluorine, chlorine and bromine; provided that where $A^9$ is Leu or Phe, $A^1$ is other than D-Nal or DL-Phe and where $A^1$ is D-Nal or DL-Phe, $A^9$ is other than Leu or Phe and the salts thereof with pharmaceutically acceptable acids.

DESCRIPTION OF THE PREFERRED EMBODIMENTS

For convenience of describing this invention, the conventional abbreviation for amino acids, peptides and their derivatives are used as generally accepted in the peptide art and as recommended by the IUPAC-IUB Commission on Biochemical Nomenclature [*European J. Biochem.*, 1984, 138 9–37].

The abbreviations for the individual amino acid residues are based on the trivial name of the amino acid, e.g. Trp is tryptophan, Gln is glutamine, His is histidine, Ala is alanine, Val valine, Gly is glycine, Leu is leucine, Phe is phenylalanine. Where the amino acid residue has isomeric forms, it is the L-form of the amino acid that is represented unless otherwise indicated by D- or DL- appearing before the amino acid symbol.

Abbreviations of the uncommon amino acids employed in the present invention are as follows:

Dpa is 2,3-diaminopropionic acid
Nal is 3-(2-naphthyl)-alanine
Thi is β-2'-thienylalanine
Tpi is 2,3,4,9 tetrahydro-1 H-pyrido-3,4-b] indole-3-carboxylic acid Peptide sequences are written according to the convention whereby the N-terminal amino acid is on the left and the C-terminal amino acid is on the right
Hca is hydrocinnamic acid
Hna is 3-hydroxy-2-naphthoic acid
Hpp is 3-(4-hydroxyphenyl)propionic acid
Mpp is 3-(4-methoxyphenyl)propionic acid
Paa is phenylacetic acid
Other abbreviations used are:
AC: acyl
Ac: acetyl
AcOH: acetic acid
BOC: tert-butoxycarbonyl
$(BOC)_2O$: di-tert-butyldicarbonate
BHA: benzhydrylamine
Bzl: benzyl
BSA: bovine serum albumin
DIC: 1,3-diisopropylcarbodiimide
DMEM: Dulbecco's modified Eagle's medium
Et: ethyl
EDTA: ethylene diamine tetraacetic acid
FCBS: fetal calf bovine serium
FMOC: 9-fluorenylmethyloxycarbonyl
For: formyl
HITES: RPMI 16 4D medium plus $10^{-8}M$ hydrocortisone, 5 ul/ml bovine insulin, 10 ug/ml human transferrin, $10^{-8}M$ β-estradiol and $3 \times 10^{-8}M$ $Na_2SeO_3$
NOBt: 1-hydroxybenzotriazole
HPLC: high-performance-liquid-chromatography
Me: methyl
MeCN: acetonitrile
MeOH: methyl alcohol
TEA: triethylamine
PBS: phosphate-buffered saline
PGlu: pyroglutamic acid
psi: a pseudo peptide bond of structure $CH_2$—NH except where the following residue has a secondary N-terminal in which case the meaning is $CH_2N$
TFA: trifluoroacetic acid
Z: benzyloxycarbonyl The most particularly preferred polypeptides in the present invention are:

| Peptide No. | Structure |
|---|---|
| 1. | NH₂—CO—Trp—Gln—Trp—Ala—Val—Gly—His—Leu-psi-Leu—NH₂ |
| 2. | D—Trp—Gln—Trp—Ala—Val—Gly—His—Leu-psi-Leu—NH₂ |
| 3. | D—Trp—Glu(MeNH)—Trp—Ala—Val—Gly—His—Leu-psi-Leu—NH₂ |
| 4. | 5F—D—Trp—Gln—Trp—Ala—Val—Gly—His—Leu-psi-Leu—NH₂ |
| 5. | D—Tpi—Gln—Trp—Ala—Val—Gly—His—Leu-psi-Leu—NH₂ |
| 6. | D—Tpi—Glu(OMe)—Trp—Ala—Val—Gly—His—Leu-psi-Leu—NH₂ |
| 7. | D—Tpi—His—Trp—Ala—Val—Gly—His—Leu-psi-Leu—NH₂ |
| 8. | D—Tpi—His(Bz)—Trp—Ala—Val—Gly—His—Leu-psi-Leu—NH₂ |
| 9. | NH₂CO—Trp—Gln—Trp—Ala—Val—Gly—His—Leu-psi-Phe—NH₂ |
| 10. | D—Trp—Gln—Trp—Ala—Val—Gly—His—Leu-psi-Phe—NH₂ |
| 11. | D—Trp—Glu(MeNH)—Trp—Ala—Val—Gly—His—Leu-psi-Phe—NH₂ |
| 12. | D—Tpi—Gln—Trp—Ala—Val—Gly—His—Leu-psi-Phe—NH₂ |
| 13. | D—Tpi—Glu(OMe)—Trp—Ala—Val—Gly—His—Leu-psi-Phe—NH₂ |
| 14. | Hca—Gln—Trp—Ala—Val—Gly—His—Leu-psi-Tpi—NH₂ |
| 15. | D—pGlu—Gln—Trp—Ala—Val—Gly—His—Leu-psi-Tpi—NH₂ |
| 16. | ⌐¯¯¯¯¯¯¯¯¯¯¯¯¯⌐<br>└—Phe—Glu—Trp—Ala—Val—Gly—His—Leu-psi-Trp—NH₂ |
| 17. | D—Phe—Gln—Trp—Ala—Val—Gly—His—Leu-psi-Tpi—NH₂ |
| 18. | D—Trp—Gln—Trp—Ala—Val—Gly—His—Leu-psi-Tpi—NH₂ |
| 19. | D—Trp—His(Bz)—Trp—Ala—Val—Gly—His—Leu-psi-Tpi—NH₂ |
| 20. | D—Trp—Glu(MeNH)—Trp—Ala—Val—Gly—His—Leu-psi-Tpi—NH₂ |
| 21. | D—Trp—Glu—(OMe)—Trp—Ala—Val—Gly—His—Leu-psi-Tpi—NH₂ |
| 22. | Tpi—Gln—Trp—Ala—Val—Gly—His—Leu-psi-Tpi—NH₂ |
| 23. | Ac—Tpi—Gln—Trp—Ala—Val—Gly—His—Leu-psi-Tpi—NH₂ |
| 24. | NH₂CO—Tpi—Gln—Trp—Ala—Val—Gly—His—Leu-psi-Tpi—NH₂ |
| 25. | Hna—Tpi—Gln—Trp—Ala—Val—Gly—His—Leu-psi-Tpi—NH₂ |
| 26. | D—Tpi—Gln—Trp—Ala—Val—Gly—His—Leu-psi-Tpi—NH₂ |
| 27. | Mpp—Gln—Trp—Ala—Gly—His—Leu-psi-Trp—NH₂ |
| 28. | D—Phe—Gln—Trp—Ala—Val—Gly—His—Leu-psi-Trp—NH₂ |
| 29. | D—Trp—Gln—Trp—Ala—Val—Gly—His—Leu-psi-Trp—NH₂ |
| 30. | D—Tpi—Gln—Trp—Ala—Val—Gly—His—Leu-psi-Trp—NH₂ |
| 31. | Mpp—Gln—Trp—Ala—Val—Gly—His—Leu-psi-Trp(For)—NH₂ |
| 32. | D—Phe—Gln—Trp—Ala—Val—Gly—His—Leu-psi-Trp(For)—NH₂ |
| 33. | D—Trp—Gln—Trp—Ala—Val—Gly—His—Leu-psi-Trp(For)—NH₂ |
| 34. | D—Tpi—Gln—Trp—Ala—Val—Gly—His—Leu-psi-Trp(For)—NH₂ |
| 35. | Tpi—Gln—Trp—Ala—Val—Gly—His—Leu-psi-Tpi—OMe |
| 36. | D—Tpi—Gln—Trp—ala—Val—Gly—His—Leu-psi-Tpi—OMe |
| 37. | NH₂CO—Tpi—Gln—Trp—Ala—Val—Gly—His—Leu-psi-Tpi—OMe |
| 38. | D—Tpi—Gln—Trp—Ala—Val—Gly—His—Leu-psi-Tpi—NHMe |
| 39. | D—Tpi—Gln—Trp—Ala—Val—Gly—His—Leu-psi-Tpi—OH |
| 40. | D—Tpi—Gln—Trp—Ala—Val—Gly—His—Leu-psi-Tpi—N₂H₂CONH₂ |

SYNTHESIS OF POLYPEPTIDES

The polypeptides of the present invention can be prepared by any techniques that are known to those skilled in the peptide art. A summary of the techniques so available can be found in M. Bodanszky, Principles of Peptide Synthesis, Springer-Verlag, Heidelberg, 1984.

The techniques of exclusively solid-phase synthesis are set forth in the textbook of J. M. Stewart and J. D. Young, Solid Phase Peptide Synthesis, Pierce Chem. Co., Rockford, Ill., 1984 (2nd. ed.) and in the review of G. Barany, et al., Int. J. Peptide Protein Res., 30, 705–739, 1987.

A particularly preferred method of preparing polypeptides and their intermediate peptides of this invention is solid phase synthesis. The support employed in the solid phase synthesis of the polypeptides in this invention is benzyhydrylamine (BHA) resin or chloromethylated polystyrene resin 1% cross-linked with divinylbenzene which are commercially available. The protecting group selected for α-amino group was tert-butoxycarbonyl (Boc-) group, which was removed at each step of synthesis. The starting material containing protected amino acid was made from a Boc amino acid coupled to BHA resin or attached to chloromethylated polystyrene resin with KF. The synthesis began at the C-terminal of polypeptide and was carried out using a manual apparatus, repeated with step-wise process of deprotection of the alpha-amino group and coupling to the next amino acid.

PURIFICATION OF POLYPEPTIDES

Polypeptides were generally purified by high performance liquid chromatography (HPLC) on a reversed phase column carried out on a Rainin HPLC System (Rainin Inc., Co., Woburn, Mass.) consisting of three Rainin Rabbit HP HPLC pumps controlled by an Apple Macintosh Plus Computer, a Rheodyne injector and a Knauer Model 87 variable wavelength UV monitor. Crude peptides (10–40 mg) are loaded on a Dynamax Macro column (2.12×250 mm) packed with spherical $C_{18}$ silica gel (pore size: 300A; particle size: 12 μm) (Rainin Inc. Co.) and eluted with linear gradient by using a solvent system consisting of (A) 0.1% TFA and (B) 0.1% TFA in 70% aqueous acetonitrile at a flow rate of 2.0 ml/min. All fractions were assessed for purity and retention time by an Analytical HPLC described at below.

The quality and the elution characteristics of crude and purified peptide were established by analytical HPLC on a Hewlett-Packard Model 1090 liquid chromatography equipped with a diode array detector set at 220 and 280 nm and a reversed phase 4.6×250 nm W-porex $C_{18}$ column (pore size: 300A, particle size: 5 μm). A flow rate of 1.2 ml/min of solvent system (A) and (B)

described as above was maintained and the separations were performed at room temperature.

In most cases, polypeptides were further purified by rechromatography on the same column with slight modification to the gradient conditions. The homogeneity of purified peptides proved to be pure over 97% in analytical HPLC.

Amino Acid Analyses

Amino acid analyses of polypepties in the present invention were performed in a Beckman 6300 amino acid analyzer, on Samples that were hydrolyzed at 110° C. for 20 hrs. in sealed, evacuated tubes with 4M methanesulfonic acid containing 0.2% 3-(2-aminoethyl)-indole. The ratios of amino acid are were as expected. The residues of Leu-$_{psi}$-Leu and Leu-$_{psi}$-Phe show absorbtion peaks with retention times of 39.93, 44.56 min., respectively. Tpi was not found after 50 minutes digestion in the analysis procedure.

Assay Procedures (A) Receptor Binding Assay

Binding of $^{125}$I-GRP(14-27) and displacement by bombesin antagonists were conducted in 24-well tissue culture plates (GIBCO) using Swiss 3T3 cells. Murine Swiss 3T3 fibroblasts were maintained by weekly passage in DMEM containing 10% FCBS and antimycotics. Cultures were incubated in 5% $CO_2$ in air at 37° C. The wells were seeded with $10^5$ cells/well (viability >95%), grown to confluence and quiescency. The binding procedure was conducted 7 days after seeding. The cells were washed 2 times with 0.5 ml of binding buffer (Dulbecco's modified Eagle's medium containing 20 nM HEPES-NaOH (pH 7.4), 0.2% BSA and 100 mcg/ml bacitracin). The cells were then incubated with 0.2 nM $^{125}$I-GRP (14-27) in the presence or absence of different concentrations of antagonists ($6 \times 10^{-11}$–$6 \times 10^{-6}$M, total volume 0.4 ml).

According to Zachary and Rozengurt (1985) and Layton et al., (1988), binding of $^{125}$I-GRP at 37° C. reached a maximum value at 30 min and decreased afterwards; so, the cells were incubated at 37° C. for 30 min. After that, the cells were washed 2 times with ice-cold (4° C.) binding buffer and 2 times with the ice-cold phosphate-buffered saline (PBS,mM): NaCl 138, KCl 2.8, Na$_2$HPO$_4$ 8, KH$_2$PO$_4$ 1.45, CaCl$_2$ 0.91, MgCl$_2$ 0.49. Washed cultures were extracted in 0.5 ml of 0.5M NaOH and transferred to tubes for counting. The wells were washed once with 0.5 ml distilled water (sterile), and the washing were added to the appropriate tubes. Then the radio-activity of the samples was counted in an automatic gamma counter (Micromedic System, Inc., Huntsville, Ala.).

The Ligand - PC computerized curve fitting program of Munson and Rodbard was used to determine the types of receptor binding, dissociation constant (Kd), association constant (Ka), the maximal binding capacity of receptors (Bmax) and half-maximal inhibition (IC$_{50}$).

IC$_{50}$ values represent concentrations of antagonists causing half-maximal inhibition of 0.2 nM GRP(14-27) stimulated growth. Dissociation constant and maximal binding capacity of $^{125}$I-GRP (14-27) in our experiments were 1.32 nm and 0.769 pm/mg protein, respectively, which were similar to those reported for $^{125}$I-GRP and $^{125}$I-Tyr$^4$-bombesin. Binding characteristics of GRP receptors on 3T3 cells in these experiments agree well with values obtained for bombesin binding to pancreatic acinar (Jensen et al., 1978) and pituitary cells (Westendorf and Schonbrunn, 1983).

GRP(14-27) inhibits binding of $^{125}$I-GRP(14-27) with IC$_{50}$ 2.32, which agrees with data from Dayton et al., (1988) 2.2 nM. The binding data of polypeptides in the present invention are listed on attached Table I below.

| Code | BINDING DATA ON 3T3 SWISS | | |
|---|---|---|---|
| | $K_a(nM^{-1})$ | $K_d(nM)$ | IC$_{50}$(nM) |
| 7. | N.D. | — | — |
| 5. | 0.129 | 8 | 9.2 |
| 12. | 0.014 | 71 | 81.65 |
| 26. | 0.045 | 22 | 25.3 |
| 17. | 0.955 | 1 | 1.2 |
| 2. | 0.095 | 10.6 | 12.19 |
| 34. | 0.0006 | 1667 | 1917.05 |
| 11. | 0.217 | 5 | 5.75 |
| 27. | 0.013 | 74.5 | 85.66 |
| 29. | 0.0019 | 526.3 | 604.9 |
| 30. | 2.54 | 4 | 5.15 |
| 28. | 0.125 | 8 | 9.16 |
| 33. | 0.002 | 556 | 639.4 |
| 18. | 0.257 | 4 | 4.6 |
| 10. | 1 | 1 | 1.15 |
| 22. | 1.012 | 0.9 | 1.14 |
| 8. | 0.014 | 71 | 82.14 |
| GRP(14-27) | 0.758 ± 0.23 | 1.32 ± 0.43 | 1.52 ± 0.7 |

$B_{max} = 7.12 \times 10^{-12}$, i.e. $0.354 \times 10^{-12}$M/mg protein
N.D.=NO DISPLACEMENT IC$_{50}$ is the concentration of unlabelled ligand that displaced half the specific radioligand binding. It is calculated according to the equation of Cheng and Prussoff (1973): IC$_{50}$=Kc (1+L/Kh), where Kc and Kh are the dissociation constants of unlabelled (cold) and labelled (hot) ligand respectively, and L is the concentration of radioligand used.

(B) Amylase Release

Isolated pancreatic acini were prepared by collagenase digestion of the pancreas obtained from male Wistar rats (150-180 g) fasted overnight. Animals were killed by cervical dislocation and the pancreas was removed and then digested by highly purified collagenase (CLSPA, 540 U/mg, Cooper Biomedical, Freehold, N.J., U.S.A.) according to the method of Amsterdam, Solomon and Jamieson (1978).

Dispersed acini were suspended in an incubation medium containing 24.5 mM HEPES, 98 mM NaCl, 4.0 mM KCl, 11.7 mM KH$_2$PO$_4$, 1.0 mM MgCl$_2$, 0.3 mM CaCl$_2$, 5.0 mM glucose, 1% (w/v) essential and nonessential amino acid mixture (Serva Feinbiochemica, Heidelberg, FRG), 2 mM glutamine, 0.2% BSA and 0.01% (w/v) trypsin inhibitor. The incubation solution was saturated with oxygen and maintained at 37° C. in a shaking bath (60 oscillations/min). Acinar suspension was incubated After incubation, tubes were centrifuged at 1000 g for 5 min and the supernatant separated from the pellet. Amylase content in the supernatant and dissolved pellet were determined separately as described by Bernfeld (1955). Amylase secretion was given as percentage increment over basal value. Incubations were duplicated. Unstimulated amylase release during the entire experimental period was determined as the basal value.

When added to the incubation medium in gradually increasing concentrations, caused a concentration-dependent inhibition of amylase release stimulated by submaximal concentration of GRP ($10^{-9}$M).

(C) Inhibition of $^3$H-Thymidine incorporation by 3T3cells.

SCLC cells were used 2 to 4 days after passage. Single cell suspensions were prepared by washing the cells (twice with PBS then pipetting them in PBS containing 0.2 g/liter glucose, 0.2 g/liter EDTA, and 14 mM lignocaine hydrochloride at 37° C. until the suspension appeared to be uniform (2–4 min). The cells were washed three times and resuspended in HITES without FCSB. Cultures were set up at $1.34 \times 10^5$ cells plated on day 0, all peptides added at same time in 1 ml. of RPMI-1640 medium plus HITES and 0.125% albumin. 48 hours later, 1 uc. of tritiated thymidine was added to each well and incubation continued for an additional 24 hours. Cells then were washed and deposited on glass filter paper and washed with ice cold 5% trichloro-acetic acid. Filter paper placed in vials containing scintillation fluid and counted for 1 minute.

TABLE II

ASSAY OF ANTAGONISTIC ANALOGS OF GASTRIN RELEASING PEPTIDE (GRP) 3T3 CELLS. INHIBITION OF INCORPORATION OF $^3$H-THYMIDINE.

| PEPTIDE ANALOG Number | ng/ml | GRP 3 ng/ml | DPM ± S.E. | % inhibition vs. GRP |
|---|---|---|---|---|
| | | | 207000 ± 4200 | |
| | | | 348000 ± 15300 (**) | |
| 26 | 50 | + | 233000 ± 8800 | 82 |
| | 500 | + | 205000 ± 12500 | >100(−1*) |
| | 1000 | + | 222000 ± 3900 | 89 |
| 17 | 50 | + | 277000 ± 9800 | 50 |
| | 500 | + | 207000 ± 3800 | 100 |
| | 1000 | + | 223000 ± 1200 | 89 |
| 5 | 50 | + | 283000 ± 5400 | 46 |
| | 500 | + | 280000 ± 21900 | 48 |
| | 1000 | + | 199000 ± 7100 | >100(−4*) |
| 10 | 50 | + | 261000 ± 19500 | 62 |
| | 500 | + | 242000 ± 8300 | 75 |
| | 1000 | + | 255000 ± 26200 | 66 |
| 22 | 50 | + | 269000 ± 14000 | 56 |
| | 500 | + | 280000 ± 14000 | 48 |
| | 1000 | + | 198000 ± 18800** | >100(−4*) |

**$P < 0.01$; (−*) Inhibition below the basal unstimulated level
$348,000 - 207,000 = 141,000$ was taken as the stimulation (D) Inhibition of growth of various small cell lung carcinomas (S.C.L.C.):

Stock culture of H-69 and H-345 S.C.L.C. cells obtained from National Cancer Institute (NCI) are maintained in suspension culture. Inhibition of GRP-induced DNA synthesis by Bombesin antagonists is performed by measuring ($^3$H) thymidine incorporation. Inhibition of GRP induced DNA synthesis by bombesin antagonists was shown to be significant and concentration dependent.

(E) The effect on pancreatic secretion in vivo

Secretory studies were carried out on 6 conscious cats (2–3 kg) prepared with chronic gastric and pancreatic fistulae as described previously (Konturek et al., 1976). Briefly, the cannula used in the gastric fistula was the type described by Emas (1960). This cannula was inserted to the pyloric gland area near the greater curvature. Pancreatic fistula was made using special T-shaped metal cannula with the lateral and main limbs as adapted by us for cats. The common bile duct was divided just before joining the pancreatic duct and transplanted to the upper duodenum to separate the bile flow from that of pancreatic juice. A small duodenal pouch containing the entrance of the major pancreatic duct was prepared and the lateral limb of the pancreatic cannula was inserted into this pouch. The main limb of the cannula was placed in the distal duodenum about 3 cm beyond the duodenoduodenostomy.

The secretory studies began about 3 months after the surgery. Food was withheld from the cages at least 18 h before each test. Throughout each test (except with feeding) the gastric fistula was left open to allow the drainage of gastric juice to the outside.

Secretion from the pancreatic fistula was collected continuously and divided into 15 min samples. The volume was recorded and protein and bicarbonate concentrations and outputs were determined as described previously (Konturek et al., 1976).

Several series of tests were performed on each animal, for comparison of the secretory potencies. GRP was infused i.v. in graded doses (1250 pmol/kg-h of GRP) in 1-day test without or with addition of Peptide 5. In tests with feeding, the gastric fistula was kept closed and each cat was offered about 50 g of cooked homogenized ground beef that was usually completely consumed. Intravenous infusion of saline (about 10 ml/h) was maintained throughout the postprandial period and when the pancreatic secretory response reached a well sustained plateau, Peptide 5 was administered and the secretion was examined for further 2 h period. In separate tests on fasted cats (without peptide infusion or meat feeding) basal pancreatic secretion (with gastric fistula open) was measured for 2 h period and then Peptide 5 (10 nmol/kg-h) was added to the infusion at a dose that completely abolished the pancreatic secretion induced by GRP. The results are set forth below.

Bombesin analogs Peptides (5), (10) and (2) were tested in vivo on serum gastrin inhibition after GRP stimulation. Eight minutes after stimulation with GRP (3 μg/100 g BW) serum gastrin levels increased from 16.7 pg/ml (control) to 105 pg/ml. Rat injected 10 min. before the GRP stimulation with a bolus of Peptides (5), (10) and (2) antagonists (30 μg/100 g BW) showed a decrease in the level of gastrin secretion (after 8 min, 36.8 pg/ml for Peptide (2); 24.2 pg/ml for Peptide (10) and 39.2 pg/ml for Peptide (5).

The bombesin/GRP antagonists of the present invention are useful for the treatment of states of hypergastrinemia, for example, prenicious anemia, chronic atrophic gastritis, Zollinger-Ellison Syndrome, and vitiligo, associated with diffuse hyperplasia of gastric enterochromaffin-like cells, and with an increased risk of developing, multifocal gastric carcinoid tumors. Furthermore, enterochromaffin-like cell hyperplasia is readily produced in animals rendered hypergastrinemic.

Such treatment is advantageous over present drugs, since H$_2$-antagonists like cimetidine which cause hypergastrinemia and may lead to carcinoid tumors in humans. In addition, cessation of therapy with H$_2$-antagonists causes an immediate recurrence of ulcers, because of existing hypergastrinemia.

Since these compounds of this invention are antagonists of bombesin/GRP receptors, they can be used in treatment of lung cancer, colon cancer and gastric cancer.

On the basis of these results above and data in rats, the peptides of the invention can be administered in the form of pharmaceutically acceptable, nontoxic salts, such as acid addition salts, illustrative of such acid addition salts are hydrochloride, hydrobromide, sulphate, phosphate, fumarate, gluconate, tannate, maleate, acetate, citrate, benzoate, succinate, alginate, pamoate, malate, ascorbate, tartrate, and the like.

Microcapsules of microparticles of these peptides formulated from poly(DL-lactide-cogylcolide) may be the preferred sustained delivery systems. Intravenous, intramuscular or subcutaneous administration in isotonic saline, phosphate buffer solutions or the like may also be used. Aerosols for pulmonary delivery may be also used.

These pharmaceutical compositions will contain the peptide in conjunction with a conventional, pharmaceutically-acceptable carrier. The dosage will be from about 1 to 1000 micrograms of the peptide per kilogram of the body weight of the host when given parenterally. Treatment of subjects with these peptides may be carried out in the same manner as the clinical treatment using other agonists and antagonists of LHRH, somatostatin analogs or other peptides.

These peptides may be administered to mammals intravenously, subcutaneously, intramuscularly, intranasally or by pulmonary aerosol to achieve gastric inhibitory or antitumor effect. Effective dosages will vary with the form of administration and the particular species of mammal being treated. An example of one typical dosage form is a physiological saline solution containing the peptide which solution is administered to provide a dose in the range of about 0.01 to 0.20 mg/kg of body weight. Sustained delivery formulations may have to be given only once as month and the duration of treatment can be several months.

Although the invention has been described with regard to its preferred embodiments, it should be understood that changes and modifications obvious to one having the ordinary skill in this art may be made without departing from the scope of the invention, which is set forth in the claims which are appended thereto. Substitutions known in the art which do not significantly detract from its effectiveness may be employed in the invention.

GENERAL OPERATIONS FOR POLYPEPTIDE SYNTHESIS COMMENCING WITH A BOC-AMINOACID-RESIN UNIT

Operation I:
(1) wash with $CH_2Cl_2$ (3×1 min);
(2) deprotection with 50% TFA in $CH_2CH_2$ twice for 5 min and 25 min respectively. For peptide resins containing D- or L-Trp or Tpi, deprotection with 50% TFA in $CH_2Cl_2$ containing 5% mercaptoethanol and 5% anisol;
(3) wash with $CH_2Cl_2$ (6×1 min);
(4) neutralization with 10% triethylamine in $CH_2Cl_2$ (2×3 min)
(5) wash with $CH_2Cl_2$ (6×1 min);
(6) coupling:
  i) addition of Boc-amino acid (3 equiv.) and HOBt (3.3 equiv.) in DMF (3 min)
  ii) addition of 20% diisopropylcarbodiimide (3 equiv.) in $CH_2Cl_2$ and shaking 60-90 minutes
(7) was with $CH_2Cl_2$ (2×1 min), ethanol (2×1 min) and $CH_2Cl_2$ (5×1 min).

Operation II:
For introduction of the reduced peptide bond: $-CH_2NH-$, the step (6) of operation (I) was modified as follows:
(1) wash with DMF (2×1 min)
(2) addition of Boc leucine aldehyde (3equiv.) in DMF containing 1% AcOH;
(3) addition of $NaBH_3CN$ (3.5 equiv.) in DMF and shaking 60 min;
(4) wash with 50% MeOH (3×1 min); 100% MeOH (3×1 min); $CH_2Cl_2$ (3×1 min).

Operation III:
For the coupling of Boc-Asn, Boc-Gln and Boc-Gly, step (6) of operation I is modified as follows:
20% diisopropylcarbodiimide (3 equiv.) in $CH_2Cl_2$ was added to a mixture DMF solution of Boc amino acid (3.0 equiv.) and HOBt (3.3 equiv.) at 0° C. for 15 min and at room temperature 15, insolubles removed by filtration, filtrate added to peptide resin, and shaken with Boc-Gln or Boc-Asn for 2-4 hours or Boc-Gly for 1. hr.

Operation IV:
The following procedures were performed for introduction of Fmoc amino acid.
(1) After deprotection and neutralization, wash with $CH_2Cl_2$ (3×1 min) and DMF (3×1 min)
(2) coupling
  i) addition of Fmoc amino acid (3 equiv.) and HOBt (3.3 equiv.) in DMF (3 min)
  ii) addition of 2% diisopropylcarbodiimide (3 equiv.) $CH_2Cl_2$ and shaking 60 min.
(3) wash with ethanol (3×1 min); DMF (3×1 min).
(4) deprotection of Fmoc-group with 50% piperidine in DMF for 30 min.
(5) wash with DMF (6×1 min)
(6) another coupling is as described at step (2).

After the desired intermediate peptides of Formula I have been prepared, the peptide resin was then treated with liquid HF in the presence of anisole to yield the polypeptide in free form wherein X of Formula I was hydrogen, and Y of Formula I was $-NH_2$ or OH; or in protected form wherein $A^2$ of Formula I is Glu (OMe) or His(Bz).

Converting a functional group at the N,C-terminal or side chain group of polypeptide from free or protected form to another N or C-terminal, or side group functional group of polypeptide was carried out with a suitable reagent in solution. For example, a protecting polypeptide containing Glu at position $A^2$ was reacted with methyl amine in the presence of DIC to obtain a polypeptide containing Glu(MeNH) at $A^2$ position. A free N-terminal polypeptide was reacted with KOCN to get a polypeptide containing $NH_2CO-$ at the X position.

In the following examples the following number coding is utilized to identify intermediates. Recode a/b/Res is the initial resin used in Example "a" step "b". The code a/b/c is a precursor for peptide "c" made in step "b" of Example "a". a, b, and c are all integers.

EXAMPLE 1

(1) A: Example of L- and D- Tpi 2.04 g (10 mM) of L-Trp was dissolved in 25 ml of boiling water containing 2.1 g of critic acid. 0.5 ml 40% formaldehyde were added and solids began to form immediately. The mixture was chilled in an ice bath and the solids collected and washed with cold water and air dry solids at room temperature, to yield 2.14 g or 99% solids m.p. with (decomposition) ca. 310°. The D-Isomer is formed in the same manner and also has m.p. (decomposition) ca. 310° C.

B. Example of L- and D- Boc-Tpi

To a stirred suspension of 10.8 g (50 mM) of D-Tpi in 250 ml of 0.2N NaOH and 7.5 ml triethyl amine was added 10 g of Di-tert-butyl dicarbonate, the mixture stirred 4 hours then another 10 g of dicarbonate added and a further 10 g after another 3 hrs. of stirring. The mixture was stirred overnight and extracted (2×100 ml) with ether, which was discarded. Citric acid was added to the aqueous layer until acid (pH 3-5). The solids were collected and washed with water and air dried overnight.

The solids were suspended in 100 ml tetrahydrofuran. Almost all solids dissolved. The insolubles were removed by filtration and THF removed under vacuum. The residue triturated with ether to yield 9.20 g or 58%. This material has same m.p. as the starting material, but differs in solubility and TLC on silica using 85:15:0.5 $CHCl_3$:MeOH:HOAc.

2.55 g of L-Tpi gives 2.22 g or 59% of Boc-Tpi using the same method.

(2) Example of Boc-Leu-CHO

Boc-Leucine methyl ester (35 g, 134 mmoles) in dry toluene (250 ml) under $N_2$ was cooled with dry ice/acetone and (150 ml) of 25% id-isobutyl-aluminum hydride in toluene were added over 30 mins. The mixture was stirred for 20 mins in a bath of dry ice/acetone after the addition of the di-isobutyl aluminum hydride, then methanol (15 ml) was added cautiously. The mixture was poured into 1000 ml ice-cold water, shaken and filtered. The toluene was separated and the aqueous phase re-extracted with ether (3×300 ml). Toluene and ether extracts were combined and dried ($Na_2SO_4$). The resulting oil was passed rapidly through a silica gel column (3×50 cm) in 1500 ml 15% EtOAc/petrol. The Boc-Leu aldehyde was obtained as an oil (27.6 g).

EXAMPLE 2

The coupling of Boc-Leu-CHO is performed as following operation (II):
(1) wash with DMF 2 times;
(2) Addition of 1.5 mmoles Boc-Leu-CHO in DMF containing 1% AcOH;
(3) Addition of 2.0 mmoles $NaBH_3CN$ in DMF and shake for 60 min;
(4) wash with 50% methanol in $H_2O$ 2 times and 100% MeOH 2 times. $CH_2Cl_2$ 3 times;

After the removal of Boc group from Boc-Leu-$psi$-Leu-BHA resin and neutralization, the coupling of Boc-His(Z) was carrie out as described as in Operation (I).

The coupling of Boc-Gly is performed as in Operation (III).

20% 1,3-diisopropylcarbodiimide (1.5 mmole) in $CH_2Cl_2$ was added to a DMF solution of 1.5 mmoles Boc-Gly and 1.65 mmoles HOBt at 0° C., stirred under cooling for 15 min and at room temperature for 15 min, the precipitate filtered off and added to resin, and shaken for 60 min.

The subsequent amino acid residues Boc-Val, Boc-Ala and Boc-Trp were then sequentially introduced by coupling in the same manner as indicated in operation (I) to yield 0.90 g protected peptide resin with a structure Boc-Trp-Ala-Val-Gly-His(Z)-Leu-$psi$-Leu-BHA resin (2/1/Res).

After incorporating Boc-Trp, the deprotection of Boc-group is performed with 50% TFA in DCM containing 5% mercaptoethanol and 5% anisol to yield TFA Trp-Ala-Val-Gly-His(Z)-Leu-psi-Leu-BHA-resin (2/2/Res).

0.91 g TFA Trp-Ala-Val-Gly-His(Z)-Leu-$psi$-Leu-BHA-resin (2/2/Res) is divided into eight portions

| Peptide # | |
|---|---|
| 1. | $NH_2CO$—Trp—Gln—Trp—Ala—Val—Gly—His—Leu-psi-Leu—$NH_2$ |
| 2. | D—Trp—Gln—Trp—Ala—Val—Gly—His—Leu-psi-Leu—$NH_2$ |
| 3. | D—Trp—Glu(MeNH)—Trp—Ala—Val—Gly—His—Leu-psi-Leu—$NH_2$ |
| 4. | 5F—D—Trp—Gln—Trp—Ala—Val—Gly—His—Leu-psi-Leu—$NH_2$ |
| 5. | D—Tpi—Gln—Trp—Ala—Val—Gly—His—Leu-psi-Leu—$NH_2$ |
| 6. | D—Tpi—Glu(OMe)—Trp—Ala—Val—Gly—His—Leu-psi-Leu—$NH_2$ |
| 7. | D—Tpi—His—Trp—Ala—Val—Gly—His—Leu-psi-Leu—$NH_2$ |
| 8. | D—Tpi—His(Bz)—Trp—Ala—Val—Gly—His—Leu-psi-Leu—$NH_2$ |

Polypeptides in the example containing same fragment Trp-Ala-Val-Gly-His-Leu-$psi$-Leu $NH_2$ but two different residues at N-terminal were built step by step on benzyhydrylamine (BHA) resin in accordance with the standard methods of solid phase synthesis.

0.50 g BHA resin (0.9 mmole $NH_2$/g) was treated with 10% TEA in $CH_2Cl_2$ (neutralization) twice each for three minutes and washed with $CH_2Cl_2$ six times. The resin was mixed with 1.35 mmole Boc-Leu and 1.50 mmoles 1-hydroxybenzotriazole (HOBt) in DMF for three minutes. 20% 1,3-diisopropylcarbodiimide (DIC) with 1.3 mmoles in $CH_2Cl_2$ was added. The mixture was shaken at room temperature for 60 minutes. The resulting Boc-Leu-BHA resin was washed with $CH_2Cl_2$, Methanol two times each, and $CH_2Cl_2$ three times, and then subjected to a Kaiser test (Anal. Biochem. 34, 595 (1970)). In case where incomplete coupling occurs, the coupling procedure is repeated.

The removal of the Boc-group (deprotection) from Boc-Leu-BHA resin was carried out in a solution of 50% TFA in DCM for 5 minutes, filtered and retreated for 25 min., and then washed with DCM six times.

Neutralization is performed as described above for the BHA resin.

(about 100 mg each) which are used to accomplish the synthesis of designed protected polypeptide resins in accordance with the procedures described at Operation I for coupling of Boc-D-Trp, Boc-5F-D-Trp, Boc-D-Tpi and Boc-His(Z) and with Operation III for Boc-Gln.

Sequential addition of Boc-Gln and Boc-Trp to above heptapeptide resin (2/2/res) gives:
2/2/01 Boc-Trp-Gln-Trp-Ala-Val-Gly-His(Z)-Leu-$psi$-Leu-BHA resin.

Sequential coupling of Boc-Gln and Boc-D-Trp to heptapeptide resin (2/2/res) gives:
2/2/02 Boc-D-Trp-Gln-Trp-Ala-Val-Gly-His(Z)-Leu-$psi$-Leu-BHA resin.

Coupling Boc-Gln and Boc-5F-D-Trp to heptapeptide resin (2/2/res) leads to:
2/2/04 Boc-5F-D-Trp-Gln-Ala-Val-Gly-His(Z)-Leu-$psi$-Leu-BHA resin.

2/2/05 Boc-D-Tpi-Gln-Trp-Ala-Val-Gly-His(Z)-Leu-$psi$-Leu-BHA resin is obtained by successive coupling of Boc-Gln and Boc-D-Tpi.

2/2/06 Boc-D-Tpi-Glu(OMe)-Trp-Ala-Val-Gly-His(Z)-Leu-$psi$-Leu-BHA resin is obtained by successive coupling of Boc-Glu(OMe) and Boc-D-Tpi.

2/2/07  Boc-D-Tpi-His(Z)-Trp-Ala-Val-Gly-His(Z)-Leu-*psi*-Leu-BHA resin is obtained by successive coupling of Boc-His(Z) and Boc-D-Tpi.

2/2/08  Boc-D-Tpi-His(Bz)Trp-Val-Gly-His(Z)-Leu-*psi*-Leu-BHA resin is obtained by successive coupling of Boc-His(Bz) and Boc-D-Tpi.

After the removal of Boc-group with 50% TFA in DCM containing 5% mercaptoethanol and 5% anisol, the Boc-deprotected polypeptide resin is washed with DCM, methanol and DCM three times each and treated with freshly distilled HF (5 ml) and anisole (0.25 ml) at 0° C. for 1 hr. The solvent is evaporated in vacuo, and washed with ether or ethylacetate then extracted with 70–80% acetic acid and lyophilized to yield crude:

2.3/01  Trp-Gln-Trp-Ala-Val-Gly-His-Leu-*psi*-Leu-NH$_2$

| Peptide # | |
|---|---|
| 2. | D—Trp—Gln—Trp—Ala—Val—Gly—His—Leu-psi-Leu—NH$_2$ |
| 4. | 5F—D—Trp—Gln—Trp—Ala—Val—Gly—His—Leu-psi-Leu—NH$_2$ |
| 5. | D—Tpi—Gln—Trp—Ala—Val—Gly—His—Leu-psi-Leu—NH$_2$ |
| 6. | D—Tpi—Glu(OMe)—Trp—Ala—Val—Gly—His—Leu-psi-Leu—NH$_2$ |
| 7. | D—Tpi—His—Trp—Ala—Val—Gly—His—Leu-psi-Leu—NH$_2$ |
| 8. | D—Tpi—His(Bz)—Trp—Ala—Val—Gly—His—Leu-psi-Leu—NH$_2$ |

A mixture of 40 mg Trp-Gln-Trp-Ala-Val-Gly-His-Leu-*psi*-LeuNH$_2$ (2/3/1) and 20 μl TEA in 0.5 ml DMF and 20 mg KOCN in 100 μl H$_2$O was stirred at 0° C., 100 μl AcOH was then dropped in the mixture and stirred at 0° C. for 1 hr. The reaction mixture was subjected purification to yield:

| Peptide # | |
|---|---|
| 1. | NH$_2$CO—Trp—Gln—Trp—Ala—Val—Gly—His—Leu-psi-Leu—NH$_2$. |

Peptide (3) was prepared by successively coupling Fmoc-Glu(OBut) and Fmoc-D-Trp by the method indicated in Operation IV to Trp-Ala-Val-His(Z)-Leu-*psi*-Leu-BHA resin (2/2/Res) yield Fmoc-D-Trp-Glu(OBut)-Trp-Ala-Val-Gly-His(Z)Leu-*psi*-Leu-BHA resin (2/4/3). The peptide resin was treated by 10% TFA in DCM containing 5% 2-mercaptoethanol for 30 min to remove the But group from the carboxyl group of Glu. After washing six times with DCM, MeNH$_2$ was bubbled through a Fmoc-D-Trp-Glu-Trp-Ala-Val-Gly-His(Z)-Leu-*psi*-Leu-BHA resin bed (2/5/Res) in 5 ml DMF at 0° C. for 5 min., 0.25 ml 20% DIC in DCM added and reacted at 0° C. for 2 hrs. The resin was then washed with DCM and the Fmoc group removed with piperidine. Peptide (3) D-Trp-Glu(MeNH)Trp-Ala-Val-Gly-His-Leu-*psi*-Leu-NH$_2$ (RC-3490) was obtained after treatment with HF.

The purification was carried by HPLC with solvent system consisting of (A) 0.1% TFA and (B) 1% TFA in 70% acetonitrile. Purified peptides are proved to be over 97% pure in analytical HPLC. The retention times of polypeptides in this example is described in the following table.

| | Analytical HPLC data | |
|---|---|---|
| Peptide No. | Gradient | |
| % B/min | on column | Retention time |
| 2. | 25–65% B/40 | 11.84 |
| 4. | 25–65% /40 | 14.85 |
| 5. | 25–65% /40 | 14.32 |
| 6. | 25–65% /40 | 19.21 |
| 7. | 30–70% /40 | 9.11 |

The results of amino acid analyses for polypeptides in this example were as expected. For example, amino acid ratios of Peptide (2) with the structure of D-Trp-Gln-Trp-Ala-Val-Gly-His-Leu-*psi*-Leu-NH$_2$ was 1.11:2.09:0.90:1.03:0.95:0.92 (Gln:Trp:Ala:Val:Gly:His). The residue of Leu-*psi*-Leu showed an absorbtion peak with retention time 39.95 min. Tpi in the Peptides (5), (6), (7) and (8) was not detected.

EXAMPLE 3

| Peptide # | |
|---|---|
| 9. | NH$_2$CO—Trp—Gln—Trp—Ala—Val—Gly—His—Leu-psi-Phe—NH$_2$ |
| 10. | D—Trp—Gln—Trp—Ala—Val—Gly—His—Leu-psi-Phe—NH$_2$ |
| 11. | D—Trp—Glu(MeNH)—Trp—Ala—Val—Gly—His—Leu-psi-Phe—NH$_2$ |
| 12. | D—Tpi—Glu—Trp—Ala—Val—Gly—His—Leu-psi-Phe—NH$_2$ |
| 13. | D—Tpi—Glu(OMe)—Trp—Ala—Val—Gly—Leu-psi-Phe—NH$_2$ |

The polypeptides in this example contain the same fragment Trp-Ala-Val-Gly-His-Leu-*psi*-PheNH$_2$. Boc-Trp-Ala-Val-Gly-His(Z)Leu-*psi*-Phe-BHA (3/1/res) resin was built step by step on 0.5 g BHA resin (0.9 mmoles NH$_2$/g) in accordance with the solid phase synthesis as described in the portion of Example (2) except that Boc-Phe is instead of Boc-Leu at the first coupling.

The partial peptide resin containing about 150 mg Boc-Trp-Ala-Val-Gly-His(Z)-Leu-*psi*-Phe-BHA resin (3/1/Res) each was coupled with other two residues according to the procedures described at Operation I for coupling of Boc-Trp, Boc-D-Trp, Boc-D-Tpi and Boc-Glu(OMe) and Operation III for Boc-Gln to yield the final polypeptide resin.

Sequential coupling of Boc-Gln and Boc-Trp to the above mentioned heptapeptide resin (3/1/res) gives:

3/2/09.  Boc-Trp-Gln-Trp-Ala-Val-Gly-His(Z)-Leu-*psi*-Phe-BHA resin.

Successive addition of Boc-Gln and Boc-D-Trp to heptapeptide resin (3/1/res) gives:

3/2/10.  Boc-D-Trp-Gln-Trp-Ala-Val-Gly-His(Z)-Leu-*psi*-Phe-BHA resin.

Coupling Boc-Gln and Boc-D-Tpi to heptapeptide resin (3/1/res) yields:

3/2/12. Boc-D-Tpi-Gln-Trp-Ala-Val-Gly-His(Z)-Leu-$_{psi}$-Phe-BHA resin.
3/2/13. Boc-D-Tpi-Glu(MeO)-Trp-Ala-Val-Gly-His(Z)-Leu-$_{psi}$-Phe-BHA resin is built by coupling of Boc-Glu(OMe) and Boc-D-Tpi to heptapeptide resin (3/1/res).

After the removal of Boc-group with 50% TFA in DCM containing 5% mercaptoethanol and 5% anisol, the polypeptide resin is washed with DCM, methanol and DCM three times each and treated with freshly distilled HF (5 ml) and anisole (0.25 ml) at 0° C. for 1 hour. The solvent is evaporated in vacuo and washed with ethylacetate, extracted with 70–80% acetic acid and lyophilized. The following polypeptides are obtained as following:

3/3/09. Trp-Gln-Trp-Ala-Val-Gly-His-Leu-$_{psi}$-Phe-NH$_2$

| Peptide # | |
|---|---|
| 10. | D—Trp—Gln—Trp—Ala—Val—Gly—His—Leu-psi-Phe—NH$_2$ |
| 12. | D—Tpi—Gln—Trp—Ala—Val—Gly—His—Leu-psi-Phe—NH$_2$ |
| 13. | D—Tpi—Glu(MeO)—Trp—Ala—Val—Gly—His—Leu-psi-Phe—NH$_2$ |

The peptide having NH$_2$CO at N-terminal was prepared by following procedure:

A mixture of 40 mg crude polypeptide (3/3/9) Trp-Gln-Trp-Ala-Val-Gly-His-Leu-$_{psi}$-Phe-NH$_2$ and 20 μl TEA in 0.5 ml DMF and 20 mg KOCN in 100 μl H$_2$O were stirred at 0° C., 100 μl AcOH was then dropped into the above mixture and the reaction kept stirring at 0° C. for 1 hr. The reaction mixture containing the desired Peptide (9) NH$_2$CO-Trp-Gln-Trp-Ala-Val-Gly-His-Leu-$_{psi}$-Phe-NH$_2$ was subjected to HPLC purification.

Peptide (11) was prepared by successively coupling two Fmoc-amino acid by the method indicated in solid-phase synthesis Operation IV.

150 mg TFA Trp-Ala-Val-Gly-His(Z)Leu-$_{psi}$-Phe-BHA resin (3/1/Res) was neutralized with 10% TEA, washed with CH$_2$Cl$_2$ and DMF, and coupled with Fmoc-Glu(OBut) to yield Fmoc-Glu(OBut)-Trp-Ala-Val-Gly-His(Z)-Leu-$_{psi}$-Phe-BHA resin (3/5/11). Fmoc-D-Trp-Glu(OBut)-Trp-Ala-Val-Gly-His(Z)-Leu-$_{psi}$-Phe-BHA resin was obtained after deprotection with 50% piperidine and coupling with Fmoc-D-Trp. The But group was removed from the Fmoc protected peptide resin by treatment with 10% TFA in DCM containing 2% mercaptoethanol for 30 min. MeNH$_2$ was bubbled through a bed of 200 mg Fmoc-D-Trp-Glu-Trp-Ala-Val-Gly-His(Z)Leu-$_{psi}$-Phe-BHA resin (3/6/11) in 5 ml DMF at 0° C. for 5 min., 0.2 ml. 20% DIC in DCM added and the mixture stirred at 0° C. for 2 hrs. The resin was then washed with DCM and the Fmoc group removed with piperidine. After treatment with HF and anisol, Peptide (11) D-Trp-Gly-MeNH)Trp-Ala-Val-Gly-His-Leu-$_{psi}$-PheNH$_2$ was subjected to purification with HPLC.

The retention times of peptides in this example is indicated in following table.

| | Analytical HPLC data | |
|---|---|---|
| Peptide No. | Gradient % B/min | Retention time on column D |
| 9. | 25–65 | 16.38 |
| 10. | 25–65 | 14.62 |
| 12. | 25–65 | 14.72 |
| 13. | 25–65 | 19.20 |

The ratios of amino acid shown by amino acid analyses were as expected. For example, the ratios of Peptide (10) D-Trp-Gln-Trp-Ala-Val-Gly-His-Leu-$_{psi}$-Phe-NH$_2$ were 1.15:0.96:0.95:1:01:0.94:1.97(Glu:Gly:Ala:Val:His:Trp) and had a peak with retention time 44.56 min. The ratios of Peptide (13) were 1.04:0.98:1.02:1.00:1.03:0.94 (Glu:Gly:Ala:Val:His:Trp) and an absorption peak of retention time 44.56 Leu-$_{psi}$-Phe. Tpi in Peptide (13) was not detected.

EXAMPLE 4

| Peptide # | |
|---|---|
| 14. | Hca—Gln—Trp—Al—Val—Gly—His—Leu-psi-Tpi—NH$_2$ |
| 15. | D-p-Glu—Gln—Trp—Ala—Val—Gly—His—Leu-psi-Tpi—NH$_2$ |
| 16. | ┌─────┐<br>└─Phe—Glu—Trp—Ala—Val—Gly—His—Leu-psi-Tpi—NH$_2$ |
| 17. | D—Phe—Gln—Trp—Ala—Val—Gly—His—Leu-psi-Tpi—NH$_2$ |
| 18. | D—Trp—Gln—Trp—Ala—Val—Gly—His—Leu-psi-Tpi—NH$_2$ |
| 19. | D—Trp—His(Bz)—Trp—Ala—Val—Gly—His—Leu-psi-Tpi—NH$_2$ |
| 20. | D—Trp—Glu(MeNH)—Trp—Ala—Val—Gly—His—Leu-psi-Tpi—NH$_2$ |
| 21. | D—Trp—Glu(OMe)—Trp—Ala—Val—Gly—His—Leu-psi-Tpi—NH$_2$ |
| 22. | Tpi—Gln—Trp—Ala—Val—Gly—His—Leu-psi-Tpi—NH$_2$ |
| 23. | Ac—Tpi—Gln—Trp—Ala—Val—Gly—His—Leu-psi-Tpi—NH$_2$ |
| 24. | NH$_2$CO—Tpi—Gln—Trp—Ala—Val—Gly—His—Leu-psi-Tpi—NH$_2$ |
| 25. | Hna—Tpi—Gln—Trp—Ala—Val—Gly—His—Leu-psi-Tpi—NH$_2$ |
| 26. | D—Tpi—Gln—Trp—Ala—Val—Gly—His—Leu-psi-Tpi—NH$_2$ |

Leu-$_{psi}$-Tpi-BHA resin is made by reacting Boc-Leu-$_{psi}$-Trp-BHA resin with formaldehyde in accordance with the procedures as follows: Boc-Leu-$_{psi}$-Trp-BHA resin is obtained from 1.0 g BHA resin (0.9 m mode NH$_2$g) with coupling Boc-Trp and Boc-Leu-CHO successively by the method indicated in Operation I and Operation II. 10 ml. DMF containing 1% acetic acid is added to the above peptide resin and then reacted with 1 ml 10% formaldehyde at room temperature for 60 minutes and washed with DMF, MeOH and DCM.

All polypeptides in this example contain a common fragment Trp-Ala-Val-Gly-His-Leu-$_{psi}$-Tpi-NH$_2$.Boc- Trp-Ala-Val-Gly-His(Z)-Leu-$_{psi}$-Tpi-BHA resin (4/1/Res) was built step by step on Leu-Psi-Tpi.BHA resin by successively coupling Boc-His(Z) (Operation I), Boc-Gly (Operation III), Boc-Val, Boc-Ala and Boc-Trp (Operation I).

A 150 mg. portion of the above intermediate peptide resin is subjected to two further couplings with the procedures described at Operation I for coupling of Hca, D-pGlu, Boc-Glu(OMe), Boc-Glu(OBz), Boc-D-Phe, Boc-D-Trp, Boc-His(Bz), Boc-Tpi, Bod-D-Tpi, AC-Tpi and Hna-Tpi and at Operation III for Boc-Gln to yield the final peptide resins.

Coupling Boc-Gln and Hca sequentially to the above mentioned heptapeptide resin (4/1/res) yields:

2/4/14/ Hca-Gln-Trp-Ala-Val-Gly-His(z)-Leu-$_{psi}$-Tpi-BHA resin.

Sequential addition of Boc-Gln and D-pGlu to heptapeptide resin (4/1/res) gives:

4/2/15. D-p-Glu-Gln-Trp-Ala-Val-Gly-His(z)-Leu-$_{psi}$-Tpi-BHA resin.

Successive coupling of Boc-Glu(OBz) and Boc-Phe to above-intermediate peptide resin (4/1/res) gives:

4/2/16. Boc-Phe-Glu(OBz)-Trp-Ala-Val-Gly-His(Z)-Leu-$_{psi}$-Tpi-BHA resin.

Coupling Boc-Gln and Boc-D-Phe to heptapeptide resin (4/1/res) yields

4/2/17. Boc-D-Phe-Gln-Trp-Ala-Val-Gly-His(Z)-Leu-$_{psi}$-Tpi-BHA resin.

4/2/18. Boc-D-Trp-Gln-Trp-Ala-Val-Gly-His(Z)-Leu-$_{psi}$-Tpi-BHA resin is built by coupling of Boc-Gln and Boc-D-Trp to heptapeptide resin (4/1/res).

4/2/19. Boc-D-Trp-His(Bz)-Trp-Ala-Val-Gly-His(Z)-Leu-$_{psi}$-Tpi-BHA resin is built by coupling of Boc-His(Bz) an Boc-D-Trp to heptapeptide resin (4/1/res).

4/2/21. Boc-D-Trp-Glu(OMe)-Trp-Ala-Val-Gly-His(Z)-Leu-$_{psi}$-Tpi-BHA resin is built by coupling of Boc-Gln(MeO) and Boc-Tpi to heptapeptide resin (4/1/res).

4/2/22. Boc-Tpi-Gln-Trp-Ala-Val-Gly-His(Z)-Leu-$_{psi}$-Tpi-BHA resin is built by coupling of Boc-Gln and Boc-Tpi to heptapeptide resin (4/1res).

4/2/23. Ac-Tpi-Gln-Trp-Ala-Val-Gly-His(Z)-Leu-$_{psi}$-Tpi-BHA resin is built by coupling of Boc-Gln and Ac-Tpi to heptapeptide resin (4/1/res).

4/2/25. Hna-Tpi-Gln-Trp-Ala-Val-Gly-His(Z)-Leu-$_{psi}$-Tpi-BHA resin is built by coupling of Boc-Gln and Hna-Tpi to heptapeptide resin (4/1/res).

4/2/26. Boc-D-Tpi-Gln-Trp-Ala-Val-Gly-His(Z)-Leu-$_{psi}$-Tpi-BHA resin is built by coupling of Boc-Glu and Boc-D-Tpi to heptapeptide resin (4/1/res).

After removal of Boc-group and treatment of the above with HF and anisol as described for Example (2) and (3), the following peptides respectively, are obtained:

| Peptide # | |
|---|---|
| 14. | Hca—Gln—Trp—Ala—Val—Gly—His—Leu-psi-Tpi—NH$_2$ |
| 15. | D—pGlu—Gln—Trp—Ala—Val—Gly—His—Leu-psi-Tpi—NH$_2$ |

4/3/16 Phe-Glu-Trp-Ala-Val-Gly-His-Leu-$_{psi}$-Tpi-NH$_2$

| Peptide # | |
|---|---|
| 17. | D—Phe—Gln—Trp—Ala—Val—Gly—His—Leu-psi-Tpi—NH$_2$ |
| 18. | D—Trp—Gln—Trp—Ala—Val—Gly—His—Leu-psi-Tpi—NH$_2$ |
| 19. | D—Trp—His(Bz)—Trp—Ala—Val—Gly—His—Leu-psi-Tpi—NH$_2$ |
| 21. | D—Trp—Glu(OMe)—Trp—Ala—Val—Gly—His—Leu-psi-Tpi—NH$_2$ |
| 22. | Tpi—Gln—Trp—Ala—Val—Gly—His—Leu-psi-Tpi—NH$_2$ |
| 23. | Ac—Tpi—Gln—Trp—Ala—Val—Gly—His—Leu-psi-Tpi—NH$_2$ |
| 25. | Hna—Tpi—Gln—Trp—Ala—Val—Gly—His—Leu-psi-Tpi—NH$_2$ |
| 26. | D—Tpi—Gln—Trp—Ala—Val—Gly—His—Leu-psi-Tpi—NH$_2$ |

20 mg Phe-Glu-Trp-Ala-Val-Gly-His-Leu-$_{psi}$-Tpi-NH$_2$ (4/3/16), 5 mg diphenylphosphoryl azide and 10 mg KHCO$_3$ in 0.5 ml DMF were stirred at 0° C. for 24 hours. The reaction mixture was subjected to purification with HPLC using solvent system 40-70% B for 60 min. to afford: Peptide (16).

Phe-Glu-Trp-Ala-Val-Gly-His-Leu-$_{psi}$-Tpi-NH$_2$ about 4.5 mg. This was pure (>95%) by analytical HPLC using solvent system 25-65% for 40 min. Retention time is min.

A mixture of 40 mg crude polypeptide 22 Tpi-Gln-Trp-Ala-Val-Gly-His-Leu-$_{psi}$-Tpi-NH$_2$, 20 μl TEA in 0.5 ml DMF and 20 mg KOCN in 100 μl H$_2$O were stirred at 0° C. A few minutes later, 100 μl AcOH was dropped into the above mixture and the reaction kept stirring at 0° C. for 1 hr. The reaction mixture containing desired (oligo)peptide: Peptide (24). NH$_2$CO-Tpi-Gln-Trp-Ala-Val-Gly-His-Leu-$_{psi}$-Tpi-NH$_2$ was subjected purification with HPLC.

Fmoc-D-Trp-Gln(OBut)-Trp-Ala-Val-Gly-His(Z)-Leu-$_{psi}$-Tpi-BHA-resin (4/2/Res) was prepared by successively coupling Fmoc-Glu(OBut) and Fmoc-D-Trp to Trp-Ala-Val-Gly-His(Z)-Leu-$_{psi}$-Tpi-BHA resin (4/1/Res) according to the method indicated in Operation IV. After removal of the But group with 10% TFA in DCM containing 2% 2-mercaptoethanol for 30 min., the peptide resin is reacted with MeNH$_2$ and DIC by the procedures described in Example (3) for the peptide resin (3/6/11) to obtain Fmoc-D-Trp-Glu(MeNH)-Trp-Ala-Val-Gly-His(Z)Leu-$_{psi}$-Tpi-BHA resin (4/3/Res). After removal of the Fmoc-Group with piperidine, the peptide resin was treated by HF (5 ml) and anisol (0.25 ml) at 0° C. for 1 hour to yield Peptide (20). D-Trp-Glu-(MeNH)-Trp-Ala-Val-Gly-His-Leu-$_{psi}$-Tpi-NH$_2$.

The retention time of peptides in this example is indicated in following table.

| | Analytical HPLC data | |
|---|---|---|
| Peptide No. | Gradient % B/min | Retention time on column D |
| 17. | 25–65/40 | 17.13 |
| 18. | 25–65/40 | 19.34 |
| 22. | 25–65/40 | 21.32 |

-continued

Analytical HPLC data

| Peptide No. | Gradient % B/min | Retention time on column D |
|---|---|---|
| 26. | 30–70/40 | 16.76 |

Amino acid analysis of peptides in this example gave the expected compositions. For example, D-Phe-Gln-Trp-Ala-Val-Gly-His-Leu-$_{psi}$-Tpi-NH$_2$ (17) had the ratios of 1.04:0.99:0.96:1.00:0.94:0.99:1.06 (Glu:Gly:Ala:Val:Phe:His:Trp). Tpi in Peptide No. 17, 24 and 26 was not shown in amino acid analysis.

EXAMPLE 5

| Peptide # | |
|---|---|
| 27. | Mpp—Gln—Trp—Ala—Val—Gly—His—Leu-psi-Trp—NH$_2$ |
| 28. | D—Phe—Gln—Trp—Ala—Val—Gly—His—Leu-psi-NH$_2$ |
| 29. | D—Trp—Gln—Trp—Ala—Val—Gly—His—Leu-psi-NH$_2$ |
| 30. | D—Tpi—Gln—Trp—Ala—Val—Gly—His—Leu-psi-NH$_2$ |
| 31. | Mpp—Gln—Trp—Ala—Val—Gly—His—Leu-psi-Trp(For)—NH$_2$ |
| 32. | D—Phe—Gln—Trp—Ala—Val—Gly—His—Leu-psi-Trp(For)—NH$_2$ |
| 33. | D—Trp—Gln—Trp—Ala—Val—Gly—His—Leu-psi-Trp(For)—NH$_2$ |
| 34. | D—Tpi—Gln—Trp—Ala—Val—Gly—His—Leu-psi-Trp(For)—NH$_2$ |

The peptides in this example contain a common fragment Gln-Trp-Ala-Val-Gly-His-Leu-$_{psi}$-Trp-NH$_2$ or Gln-Trp-Ala-Val-Gly-His(Z)-Leu-$_{psi}$-Trp(For)-NH$_2$. Boc-Gln-Trp-Ala-Val-Gly-His-Leu-$_{psi}$-Trp(For)-BHA resin (5/1/Res) is built in 1.0 g. BHA resin (0.9 m mmoles NH$_2$/g) by the successive coupling with solid phase synthesis operations as described at Example (2) except that Boc-Trp(For) instead of Boc-Leu at the first coupling. 250 mg portions of the above peptide resins are used to accomplish the synthesis of following four protected peptide resin by the final coupling with MPP, Boc-D-Phe, Boc-D-Trp or Boc-D-Tpi, respectively, according to the procedure described at Operation I.

5/2/27. Mpp-Gln-Trp-Ala-Val-Gly-His(2)-Leu-$_{psi}$-Trp(For)-BHA resin
5/2/28. Boc-D-Phe-Gln-Trp-Ala-Val-Gly-His(Z)-Leu-$_{psi}$-p(For)-BHA resin
5/2/29. Boc-D-Trp-Gln-Trp-Ala-Val-Gly-His(Z)-Leu-$_{psi}$-Trp(For)-BHA resin
5/2/30. Boc-D-Tpi-Gln-Trp-Ala-Val-Gly-His(Z)-Leu-$_{psi}$-Trp(For)-BHA resin After the removal of Boc-group with 50% TFA in DCM containing 5% mercaptoethanol and 5% anisol, the half of each of the above peptide resins were treated with HF (5 ml) and anisol (0.25 ml) at 0° C. for 1 hour to yield peptides as follows:

| Peptide # | |
|---|---|
| 31. | Mpp—Gln—Trp—Ala—Val—Gly—His—Leu-psi-Trp(For)—NH$_2$ |
| 32. | D—Phe—Gln—Trp—Ala—Val—Gly—His—Leu-psi-Trp(For)—NH$_2$ |
| 33. | D—Trp—Gln—Trp—Ala—Val—Gly—His—Leu-psi-Trp(For)—NH$_2$ |
| 34. | D—Tpi—Gln—Trp—Ala—Val—Gly—His—Leu-psi-Trp(For)—NH$_2$ |

The remaining half of each of the peptide resin were treated with HF consisting 5% anisol and 5% dimercaptethanol at 0° C. for 1 hr to yield Peptides as follows:

| Peptide # | |
|---|---|
| 27. | Mpp—Gln—Trp—Ala—Val—Gly—His—Leu-psi-Trp—NH$_2$ |
| 28. | D—Phe—Gln—Trp—Ala—Val—Gly—His—Leu-psi-Trp—NH$_2$ |
| 29. | D—Trp—Gln—Trp—Ala—Val—Gly—His—Leu-psi-Trp—NH$_2$ |
| 30. | D—Tpi—Gln—Trp—Ala—Val—Gly—His—Leu-psi-Trp—NH$_2$ |

Those peptides were purified with HPLC and the retention times are indicated in following table:

| Peptide No. | Analytical HPLC data | |
|---|---|---|
| | Gradient % B/min | Retention time on column D |
| 27. | 25–65 | 27.89 |
| 28. | 25–65 | 18.70 |
| 29. | 25–65 | 19.70 |
| 30. | 25–65 | 20.26 |
| 31. | 25–65 | 28.00 |
| 32. | 25–65 | 19.10 |
| 33. | 25–65 | 19.01 |
| 34. | 25–65 | 17.70 |

The data of amino acid analysis for peptides in this example were as expected. For example, (28) has amino acid ratios of 0.98:0.92:1.03 :0.97:0.98:1.09 (Gly:Ala:Val:Phe:His:Trp). Tpi in (30) and (34) were not shown.

EXAMPLE 6

| Peptide # | |
|---|---|
| 35. | Tpi—Gln—Trp—Ala—Val—Gly—His—Leu-psi-Tpi—OMe |
| 36. | D—Tpi—Gln—Trp—Ala—Val—Gly—His—Leu-psi-Tpi—OMe |
| 37. | NH$_2$CO—Tpi—Gln—Trp—Ala—Val—Gly—His—Leu-psi-Tpi—OMe |
| 38. | D—Tpi—Trp—Ala—Val—Gly—His—Leu-psi-Tpi—NHMe |
| 39. | D—Tpi—Trp—Ala—Val—Gly—His—Leu-psi-Tpi—OH |

| Peptide # | |
|---|---|
| 40. | D—Tpi—Trp—Ala—Val—Gly—His—Leu-psi-Tpi—N$_2$H$_2$CONH$_2$ |

Boc-Trp-OCH$_2$-resin is used as starting material which is made by following procedure: A mixture of ClCH$_2$-resin (1.0 g, 0.7 mmoles Cl/g), Boc-Trp (2.0 Trp mmoles) and KF (4 mmoles) in 20 ml DMF were stirred at 70°–80° C. for 4 hrs. The Boc-Trp-OCH$_2$ resin was then washed two times each with MeOH, H$_2$O, MeOH, DMF and DCM. Boc-Leu-$_{psi}$-Trp-OCH$_2$-resin is obtained by coupling of Boc-Leu-CHO to Trp-OCH$_2$-resin with the Operation II. Boc-Leu-$_{psi}$-Tpi-OCH$_2$-resin is obtained by the reaction of Boc-Leu-$_{psi}$-Trp-OCH$_2$resin with formaldehyde according to the procedure described in Example (4). By successive coupling of Boc-His(Z), Boc-Gly-Boc, Val-Boc-Ala-Boc-Trp and Boc-Gln with solid phase synthesis operations described as before, 1.60 g Boc-Gln-Trp-Ala-Val-Gly-His(Z)-Leu-$_{psi}$-Tpi-OCH$_2$ resin (6/1/Res) is obtained. A part of above intermediate peptide resin was used to yield Boc-Tpi-Gln-Trp-Ala-Val-Gly-His(Z)-Leu-$_{psi}$-Tpi-OCH$_2$-resin (6/2/35) by coupling of Boc-Tpi. Another aliquot of peptide resin was used to yield Boc-D-Tpi-Gln-Trp-Ala-Val-Gly-His(Z)Leu-$_{psi}$-Tpi-OCH$_2$-resin 6/2/36 by coupling Boc-D-Tpi.

After the removal of Boc-group with 50% TFA in DEM containing 5% mercaptoethanol and 5% anisol, the transesterification procedure was carried out as follows: 0.5 g Tpi-Gln-Trp-Ala-Val-Gly-His(Z)-Leu-$_{psi}$-Tpi-OCH$_2$-resin (6/3/35), methanol (15 ml) DMF (15 ml) and diisopropylethylamine (3 ml) were added and the mixture stirred at room temperature for 3 days. The resin was washed with DMF (3 times) and methanol (3 times). The filtrate and washings were combined and evaporated by rotary evaporation in vacuo to remove the solvents. After treatment with HF and anisol, 123 mg of crude Peptide (35) Tpi-Gln-Trp-Ala-Val-Gly-His-Leu-$_{psi}$-Tpi-OCH$_3$ was obtained. Peptide (36) D-Tpi-Gln-Trp-Ala-Val-Gly-His(z)-Leu-$_{psi}$-Tpi-OCH$_3$ was obtained by the same procedure but starting with (6/2/36).

A mixture of Tpi-Gln-Trp-Ala-Gly-His-Leu-$_{psi}$-Tpi-OCH$_3$(35) (40 mg), 20 µl TEA in 0.5 ml DMF and 50 mg KOCN in 100 µl H$_2$O were stirred at 0° C., a few minutes later, 50 µl AcOH was added to the mixture and reacted at 0° C. for 1 hr. The mixture is then subjected purification to yield Peptide (37) NH$_2$CO-Tpi-Gln-Trp-Ala-Val-His-Leu-$_{psi}$-Tpi-OCH$_3$.

A mixture of D-Tpi-Gln-Trp-Ala-Val-Gly-His(Z)-Leu-$_{psi}$-TpiOCH$_3$ (36) and a 1:2 w/w solution of methylamine in methanol (2 ml) was stirred at room temperature for 16 hrs. After evaporation by rotary evaporation in vacuo, the residue material was freeze dried and treated with HF and anisol. The product was Peptide (38) D-Tpi-Gln-Trp-Ala-Val-Gly-His-Leu-$_{psi}$-Tpi-NHCH$_3$ which was subjected to purification by HPLC.

Another portion of D-Tpi-Gln-Trp-Ala-Val-Gly-His(Z)-Leu-$_{psi}$-Tpi-OCH$_2$ resin (6/2/35) was treated with HF and anisol to yield: Peptide (39) D-Tpi-Gln-Trp-Ala-Val-Gly-His-Leu-$_{psi}$-Tpi-OH.

A mixture of Peptide 39 (40 mg), (Boc)$_2$O (20 mg) and TEA (20 µl) in 0.5 ml DMF were stirred at 0° C. for 4 hrs and lyophilized. After washing with ether, the residue, HOBt (10 mg) and N$_2$H$_3$CONH$_2$ (20 mg) were reacted with DCI (100 µl 20% DCI in DCM) at 0° C. overnight, the DMF evaporated, washed with ether, and the Boc-group removed with 50% TFA containing 5% mercaptoethanol and anisol to yield crude Peptide (40) D-Tpi-Gln-Trp-Ala-Val-Gly-His-Leu-$_{psi}$-Tpi-N$_2$N$_2$CONH$_2$.

We claim:

1. A nonapeptide moiety of formula I:

X-A$^1$-A$^2$-A$^3$-A$^4$-A$^5$-A$^6$-A$^7$-A$^8$-$_{psi}$-A$^9$-Q wherein
Q is NH$_2$ or OQ$^1$ where Q$^1$ is hydrogen, C$_{1-10}$ alkyl, phenyl or phenyl-C$_{7-10}$-alkyl;
X is hydrogen or a single bond linking to A$^2$, the acyl residue of an organic acid, or a group of formula R$^1$CO— wherein
 (1) R$^1$ is hydrogen, C$_{1-10}$ alkyl, phenyl or phenyl-C$_{7-10}$-alkyl;
 (2) R$^1$CO— is $$\begin{array}{c} R^2 \\ \phantom{R}\diagdown \\ \phantom{RR}N-CO- \\ \phantom{R}\diagup \\ R^3 \end{array}$$ (a)

wherein R$^2$ is hydrogen, C$_{1-10}$ alkyl, phenyl or phenyl-C$_{7-10}$-alkyl, R$^3$ is hydrogen or C$_{1-10}$ alkyl;
 (b) R$^4$-O-CO- wherein R$^4$ is C$_{1-10}$alkyl, phenyl or phenyl-C$_{7-10}$-alkyl;
A$^1$ is D-, L- or DL- pGlu, Nal, Phe, Thi, Tyr, Tpi, Hca, Hpp, Mpp, Trp or Trp substituted in the benzene ring by one or more members selected from the group consisting of halogen, NO$_2$, NH$_2$, OH, C$_{1-3}$ alkyl and C$_{1-3}$ alkoxy wherein halogen is fluorine, chlorine or bromine;
A$^2$ is Asn, Dpa, Gln, His, MeHis, His(Bz), His(Z) or a group of formula Dpa (X), Asp (Y), Glu [—] and Glu (Y); wherein
X is as above,
Y is —OR$^5$ or —N$\diagdown^{R^6}_{R^7}$ wherein
R$^5$ is hydrogen, C$_{1-3}$ alkyl or phenyl;
R$^6$ is hydrogen or C$_{1-3}$ alkyl;
R$^7$ is hydrogen, C$_{1-3}$ alkyl or —NHCONH$_2$ and
[—] is a single bond linking the side carboxyl group with the alpha amino group of A$^1$ where X is a single bond,
A$^3$ is Nal, Pal, Tpi, Trp, MeTrp, Trp(For) or Trp substituted in the benzene ring by one or more members selected from the group consisting of halogen, NO$_2$, NH$_2$, OH, C$_{1-3}$ alkyl and C$_{1-3}$ alkoxy wherein halogen is fluorine, chlorine and bromine;
A$^4$ is Ala, MeAla or Gln;
A$^5$ is Val or MeVal;
A$^6$ is Gly, Phe or D-Ala;
A$^7$ is His, MeHis, His(Bz), His(Z), Lys(Z) or Pal;
A$^8$ is a reduced isostere of Leu or Phe;
A$^9$ is Leu, Phe, Tpi, Trp or Trp substituted in the benzene ring by one or more members selected from the group consisting of halogen, NO$_2$, NH$_2$, OH, C$_{1-3}$ alkyl and C$_{1-3}$ alkoxy wherein halogen is fluorine, chlorine bromine; provided that where A$^9$ is D- or L-Leu or D- or L-Phe is other than D- or L-pGlu D-Nal or D-Phe and where A$^1$ is D-Nal D- or L-pGlu or D-Phe, A$^9$ is other than D- or L-Leu or D- or L-Phe and the salts thereof with pharmaceutically acceptable acids.

2. A polypeptide according to claim 1 of formula selected from the group consisting of
D-Trp-Gln-Trp-Ala-Val-Gly-His-Leu-$_{psi}$-Leu-NH$_2$
D-Trp-Gln-Trp-Ala-Val-Gly-His-Leu-$_{psi}$-Phe-NH$_2$
D-Trp-Glu(MeNH)-Trp-Ala-Val-Gly-His-Leu-$_{psi}$-Phe-NH$_2$, and
D-Trp-Gln-Trp-Ala-Val-Gly-His-Leu-$_{psi}$-Trp-NH$_2$.

3. A polypeptide according to claim 1 of formula D-Tpi-Gln-Trp-Ala-Val-Gly-His-Leu-$_{psi}$-Leu-NH$_2$.

4. A polypeptide according to claim 1 of formula D-Tpi-Gln-Trp-Ala-Val-Gly-His-Leu-$_{psi}$-Phe-NH$_2$.

5. A polypeptide according to claim 1 of formula D-Tpi-Gln-Trp-Ala-Val-Gly-His-Leu-$_{psi}$-Trp-NH$_2$.

6. A polypeptide according to claim 1 of formula D-pGlu-Gln-Trp-Ala-Val-Gly-His-Leu-$_{psi}$-Tpi-NH$_2$.

7. A polypeptide according to claim 1 of formula D-Phe-Gln-Trp-Ala-Val-Gly-His-Leu-$_{psi}$-Tpi-NH$_2$.

8. A polypeptide according to claim 1 of formula D-Trp-Gln-Trp-Ala-Val-Gly-His-Leu-$_{psi}$-Tpi-NH$_2$.

9. A polypeptide according to claim 1 of formula Tpi-Gln-Trp-Ala-Val-Gly-His-Leu-$_{psi}$-Tpi-NH$_2$.

10. A polypeptide according to claim 1 of formula selected from the group consisting of NH$_2$CO-Tpi-Gln-Trp-Ala-Val-Gly-His-Leu-$_{psi}$-Tpi-NH$_2$ and ACY-Tpi-Gln-Trp-Ala-Val-Gly-His-Leu-$_{psi}$-Tpi-NH$_2$ wherein ACY is acetyl, octanoyl or 3-hydroxy-2-naphthoyl.

11. A polypeptide according to claim 1 of formula D-Tpi-Gln-Trp-Ala-Val-Gly-His-Leu-$_{psi}$-Tpi-NH$_2$.

12. A polypeptide according to claim 1 of formula D-Trp-Glu(OMe)-Trp-Ala-Val-Gly-His-Leu-$_{psi}$-Tpi-NH$_2$.

13. A polypeptide according to claim 1 of formula D-Trp-Glu(MeNH)-Trp-Ala-Val-Gly-His-Leu-$_{psi}$-Tpi-NH$_2$.

14. A polypeptide according to claim 1 of formula D-Trp-His(Bz)-Trp-Ala-Val-Gly-His-Leu-$_{psi}$-Tpi-NH$_2$.

15. A polypeptide according to claim 1 of formula Phe-Glu-Trp-Ala-Val-Gly-His-Leu-$_{psi}$-Tpi-NH$_2$.

16. A pharmaceutically acceptable addition salt of a polypeptide according to claim 1.

17. A pharmaceutical composition which comprises a polypeptide of claim 1, or a therapeutically acceptable addition salt form and a pharmaceutically acceptable liquid or solid carrier thereof.

18. A method of treating cancer in a mammal which comprises administering to said mammal an effective dose of a polypeptide of claim 1, or its therapeutically acceptable addition salt thereof.

19. A polypeptide according to claim 1 in which
$A^8$ is a reduced isostere of Leu and
$A^9$ is D-, L- or DL-Tpi, Trp, or Trp substituted in the benzene ring by one or more members selected from the group consisting of halogen, NO$_2$, NH$_2$, OCH$_{1-3}$ alkyl and C$_{1-3}$ alkoxy wherein halogen is fluorine, chlorine and bromine.

20. A polypeptide according to claim 1 wherein $A^1$ is D-, L- or DL-Tpi or $A^9$ is D-, L- or DL-Tpi.

* * * * *